US008552033B2

(12) United States Patent
Hachtel et al.

(10) Patent No.: US 8,552,033 B2
(45) Date of Patent: Oct. 8, 2013

(54) INHIBITORS OF CXCR2

(75) Inventors: Stephanie Hachtel, Frankfurt (DE); Juergen Dedio, Frankfurt (DE); Stephen Shimshock, Hillsborough, NJ (US); Carolina Lanter, Audubon, PA (US)

(73) Assignee: SANOFI, Paris (FR)

( * ) Notice: Subject to any disclaimer, the term of this patent is extended or adjusted under 35 U.S.C. 154(b) by 729 days.

(21) Appl. No.: 12/337,107

(22) Filed: Dec. 17, 2008

(65) Prior Publication Data

US 2009/0215827 A1    Aug. 27, 2009

Related U.S. Application Data

(63) Continuation of application No. PCT/EP2007/005574, filed on Jun. 25, 2007.

(30) Foreign Application Priority Data

Jun. 28, 2006   (EP) .................... 06013322

(51) Int. Cl.

| A61K 31/4535 | (2006.01) |
|---|---|
| A61K 31/428 | (2006.01) |
| A61K 31/381 | (2006.01) |
| A61K 31/382 | (2006.01) |
| A61K 31/351 | (2006.01) |
| A61K 31/341 | (2006.01) |
| A61K 31/195 | (2006.01) |
| A61K 31/196 | (2006.01) |
| C07D 409/12 | (2006.01) |
| C07D 277/64 | (2006.01) |
| C07D 335/02 | (2006.01) |
| C07D 333/38 | (2006.01) |
| C07D 307/24 | (2006.01) |
| C07D 309/14 | (2006.01) |
| C07C 57/62 | (2006.01) |
| C07C 61/40 | (2006.01) |

(52) U.S. Cl.
USPC ........... 514/336; 514/367; 514/432; 514/447; 514/459; 514/472; 514/563; 546/280.4; 548/180; 549/28; 549/69; 549/424; 549/480; 562/450; 562/455

(58) Field of Classification Search
None
See application file for complete search history.

(56) References Cited

U.S. PATENT DOCUMENTS

| 4,962,224 A | 10/1990 | Wrobel et al. |
|---|---|---|
| 4,994,477 A | 2/1991 | Kempf et al. |
| 7,919,628 B2 | 4/2011 | Hachtel et al. |
| 2002/0123522 A1 | 9/2002 | Fritz et al. |
| 2004/0204417 A1 | 10/2004 | Perez et al. |
| 2005/0059705 A1 | 3/2005 | Mjalli et al. |
| 2008/0090854 A1 | 4/2008 | Hachtel et al. |

FOREIGN PATENT DOCUMENTS

| EP | 1676834 | 7/2006 |
|---|---|---|
| FR | 2825706 | 12/2002 |
| WO | WO9907351 | 2/1999 |
| WO | WO01/58852 | 8/2001 |
| WO | WO2004/108681 | 12/2004 |
| WO | WO2005/023818 | 3/2005 |
| WO | WO2005/033102 | 4/2005 |
| WO | WO2005/051940 | 6/2005 |
| WO | WO2005/070906 | 8/2005 |
| WO | WO2006/040646 | 4/2006 |
| WO | WO2006/052722 | 5/2006 |
| WO | WO2006/099610 | 9/2006 |

OTHER PUBLICATIONS

Kubinyi (3D QSAR in Drug Design: Ligand-Protein Interactions and Molecular Similarity, vol. 2-3, Springer, 1998, 800 pages).*
Huff et al., J. Med. Chem. 34(8) 1991, p. 2305-2314.*
The Merck Manual (16th Ed., 1999, pp. 52-55).*
Johnson et al. "Relationships between drug activity in NCI preclinical in vitro and in vivo models and early clinical trials." British Journal of Cancer (2001), 84(10), 1424-1431.*
Lala et al. "Role of nitric oxide in tumor progression: Lessons from experimental tumors." Cancer and Metastasis Reviews (1998), 17(1), 91-106.*
Sausville et al. "Contributions of Human Tumor Xenografts to Anticancer Drug Development." Cancer Res. 2006, 66(7), Apr. 1, 2006.*
Golub et al. "Molecular Classification of Cancer: Class Discovery and Class Prediction by Gene Expression Monitoring." Science (1999), vol. 286, 531-537.*
Boschelli et al., Inhibition of E-Selectin-, ICAM-I-, and VCAM-1-Mediated Cell Adhesion by Benzo(b)thiophene-, Benzofuran-. Indole. and Naphhalene-2-carboxamides: Identification of PD 144795 as a Antiinflammatory Agent, J. Med. Chem., 1995, pp. 4597-4614, vol. 38.
CAPLUS Abstract of: Jodlbauer et al. (J. Chromatography, A (2002), 945(1-2), 45-63).
Kubinyi (3D QSAR in Drug Design: Ligand-Protein Interactions and Molecular Similarity, vol. 2-3, Springer, 1998, 800 pages); pp. 243-244 provided.
International Search Report dated Mar. 29, 2006 corresponding to International Application No. PCT/EP2005/013624 from related U.S. Appl. No. 13/079,522.
U.S. Office Action dated Nov. 18, 2011 received in related U.S. Appl. No. 13/079,522.
Wermuth, The Practice of Medicinal Chemistry, 2d ed., 768 pages, Chapters 9-10 provided, (2003).

(Continued)

Primary Examiner — Alicia L Otton
(74) Attorney, Agent, or Firm — Scully, Scott, Murphy & Presser, P.C.

(57) ABSTRACT

The invention relates to compounds of the formula I in which R1, R2, X, A, B and Y1 to Y4 have the meanings indicated in the claims, and/or a pharmaceutically acceptable salt and/or a prodrug thereof. Because of their properties as inhibitors of chemokine receptors, especially as CXCR2 inhibitors, the compounds of the formula I and the pharmaceutically acceptable salts and prodrugs thereof are suitable for the prevention and treatment of chemokine mediated diseases.

10 Claims, No Drawings

(56) References Cited

OTHER PUBLICATIONS

International Search Report dated Oct. 2, 2007 corresponding to International Application No. PCT/EP2007/005576 from related U.S. Appl. No. 12/337,040.

U.S. Office Action dated Jan. 12, 2012 received in related U.S. Appl. No. 12/337,040.

U.S. Office Action dated Sep. 26, 2011 received in related U.S. Appl. No. 12/337,040.

Van den Eynde et al., Database Caplus Chemical Abstracts Service, Columbus, Ohio, US; Database Accession No. 1972:47393, Abstract, DE 2108189, Sep. 9, 1971.

International Search Report dated Sep. 14, 2007 corresponding to International Application No. PCT/EP2007/005574.

International Search Report dated Sep. 3, 2007 corresponding to International Application No. PCT/EP2007/005575 from related U.S. Appl. No. 12/337,970.

U.S. Final Office Action dated Feb. 8, 2012 received in related U.S. Appl. No. 12/337,970.

U.S. Office Action dated Sep. 15, 2011 received in related U.S. Appl. No. 12/337,970.

International Search Report dated Sep. 3, 2007 corresponding to International Application No. PCT/EP2007/005577 from related U.S. Appl. No. 12/337,980.

U.S. Final Office Action dated Mar. 22, 2012 received in related U.S. Appl. No. 12/337,980.

U.S. Office Action dated Nov. 2, 2011 received in related U.S. Appl. No. 12/337,980.

* cited by examiner

INHIBITORS OF CXCR2

Chemokines are a family of low molecular weight proteins (8-13 kDa) that are classified into four distinct groups depending on the positioning of the cysteine motif at the amino terminus. The family members comprise CXC, CC, XC, and CX3C chemokines of which CXC and CC are the largest and most characterized. The CXC chemokines include interleukin-8 (IL-8), neutrophil-activating protein-2 (NAP-2), growth-related oncogenes GRO-α, GRO-β, GRO-γ, epithelial cell-derived neutrophil activating factor-78 (ENA-78), granulocyte chemoattractant protein-2 (GCP-2), γ-interferon-inducible protein-10 (γIP-10), interferon-inducible T cell α-chemoattractant (I-TAC), monokine induced by γ-interferon (Mig) and platelet factor-4 (PF-4). CC chemokines include RANTES (regulated on activation normal T cell expressed and secreted), macrophage inflammatory proteins MIP-1α, MIP-1β, monocyte chemoattractant proteins MCP-1, MCP-2, MCP-3 and eotaxin. The XC family comprises two members, lymphotactin-α and lymphotactin-β, and the CX3C family consists only of a single chemokine named fractalkine (Murphy et al., Pharmacol. Rev. 52: 145-176, 2000).

Chemokines mediate their biological effects by binding to cell surface molecules, which belong to the superfamily of seven-transmembrane spanning receptors that signal through coupling to heterotrimeric G proteins. Although most chemokine receptors recognize more than one chemokine, they are almost always restricted to a single subclass. Chemokine receptor binding initiates a cascade of intracellular events of which the first step is the binding of the receptor by its high-affinity ligand. This induces a conformational change leading to a dissociation of the receptor-associated heterotrimeric G proteins into α and βγ subunits. These G protein subunits are able to activate various effector proteins, including phospholipases leading to generation of inositol trisphosphate, an increase in cytosolic calcium, and activation of protein kinases. This cascade of intracellular events mediates a wide range of functions in different leukocytes such as chemotaxis, degranulation, oxidative burst, phagocytosis, and lipid mediator synthesis.

Interleukin-8 (IL-8) is a key mediator of immunological reactions in inflammatory disorders such as atherosclerosis, ischemia/reperfusion injury, rheumatoid arthritis, chronic obstructive pulmonary disease, respiratory distress syndrome, asthma, cystic fibrosis, and psoriasis (Bizarri et al., Curr. Med. Chem. 2: 67-79, 2003). IL-8 is the most characterized member of the CXC subfamily of chemokines. Leukocyte responses to IL-8 are mediated via specific cell surface receptors, CXCR1 and CXCR2. Whereas CXCR1 is selectively activated by IL-8, CXCR2 responds to several additional chemokines including growth-related oncogenes GRO-α, GRO-β, GRO-γ, neutrophil-activating protein-2 (NAP-2), epithelial cell-derived neutrophil activating factor-78 (ENA-78), and granulocyte chemoattractant protein-2 (GCP-2). The common denominator shared by all chemokines that activate CXCR2 is a Glu-Leu-Arg (ELR) sequence in the amino terminus, which appears to serve as a recognition sequence for receptor binding and activation (Herbert et al., J. Biol. Chem. 266: 18989-18994, 1991).

Early investigations concentrated on the effect of IL-8 on neutrophils, which respond to IL-8 with calcium mobilization, actin polymerization, enzyme release, chemotaxis, and the respiratory burst. Despite similar affinities for IL-8 and similar receptor numbers of CXCR1 and CXCR2 on neutrophils, both receptors are functionally different. Responses such as calcium mobilization and the release of granule enzymes are mediated through both receptors, whereas the respiratory burst and the activation of phospholipase D depend exclusively on stimulation of CXCR1 (Jones et al., Proc. Natl. Acad. Sci. USA 93: 6682-6686, 1996). Due to their prominent role in neutrophil recruitment, CXCR1 and CXCR2 are thought to be important in several acute neutrophil-mediated diseases such as acute respiratory distress syndrome and ischemia/reperfusion injuries, as well as in chronic diseases such as asthma, psoriasis, dermatitis, and arthritis.

It has been shown that CXCR2 is also expressed by monocytes. Despite IL-8's inactivity in monocyte chemotaxis assay, this factor induces calcium flux and respiratory burst in monocytes and enhances adhesion of monocytes in static assays. Similarly, GRO-α enhances adhesion of monocytes to stimulated endothelial cells.

Moreover, IL-8 is able to induce firm arrest of monocytes on endothelial cells under conditions of physiological flow (Gerszten et al., Nature 398: 718-723, 1999). Since CXCR2 is strongly expressed on monocytes and macrophages in atherosclerotic lesions where it is suggested to play a key role in chemoattraction, retension, expansion, and activation of monocytes and macrophages, this strongly suggests that CXCR2 and one or more of its ligands (IL-8, GRO-α) play a pathophysiological role in atherosclerosis (Huo et al., J. Clin. Invest. 108: 1307-1314, 2001).

Apart from neutrophils and monocytes, numerous cell types have been shown to express IL-8 receptors. These cell types include neurons, various cancer cells, keratinocytes, and endothelial cells. Several lines of evidence indicate that IL-8 plays a direct role in angiogenesis via stimulation of CXCR2 expressed on endothelial cells. IL-8 has been shown to bind specifically to endothelial cells and induce chemotaxis. IL-8 is able to induce neovascularization in the absence of inflammatory responses (Koche et al., Science 258: 1798-1801, 1992). Moreover, there is accumulating evidence that IL-8 could play a key role in melanoma progression and metastasis as patients with melanoma metastases have elevated serum levels of IL-8. IL-8 is supposed to act as an autocrine growth and metastatic factor for melanoma cells (Schadendorf et al., J. Immunol: 151-157, 1993).

Due to the wide range of actions of IL-8, such as attraction and activation of neutrophils and monocytes/macrophages as well as promotion of endothelial cell proliferation and cancer cell growth, the inhibition of chemokine receptors CXCR1 and CXCR2 is expected to be beneficial in the prevention and treatment of numerous diseases. Besides acute and chronic inflammatory diseases such as atherosclerosis, ischemia/reperfusion injuries, chronic obstructive pulmonary disease, asthma, and rheumatoid arthritis, chemokine (such as, but not limited to IL-8, GRO-α, GRO-β, GRO-γ, NAP-2, ENA-78, or GCP-2) mediated diseases include adult respiratory distress syndrome, inflammatory bowel disease, ulcerative colitis, Crohn's disease, atopic dermatitis, cystic fibrosis, psoriasis, multiple sclerosis, angiogenesis, restenosis, osteoarthritis, septic shock, endotoxic shock, gram negative sepsis, toxic shock syndrome, stroke, glomerulonephritis, thrombosis, graft vs. host reaction, allograft rejections, alzheimers disease, malaria, viral infections, traumatic brain injury, pulmonary fibrosis, and cancer.

EP 1 676 834 A1 (Sanofi-Aventis) describes fused bicyclic carboxamide derivatives for use as CXCR2 inhibitors. WO 2006/099610 (Wyeth) describes methods for identifying therapeutic targets for the treatment of vulvovaginal atrophy by using heterocyclic compounds including chinolin and isochinolin derivatives. WO 2005/070906 (Novartis) describes benzoimidazole derivatives as inhibitors of CXCR2 receptors.

The invention provides novel compounds represented by the formula I and pharmaceutically acceptable salts, solvates, isomers or prodrugs thereof, which are inhibitors of chemokine receptors, in particular of CXC-chemokine receptors, more particular of CXCR2, and therefore useful for the prevention and treatment of chemokine mediated diseases.

The invention relates to a compound of formula I wherein

X is —CR3═CR4-, —CR5═N—, —N═CR6-, —NR7- or —S—;

R3, R4, R5 and R6
are, independently of one another, hydrogen, F, Cl, Br, I, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 1, 2, 3, 4, 5 or 6 carbon atoms, in which 1, 2, 3, 4, 5, 6, 7, 8, 9, 10, or 11 hydrogen atoms may be substituted by fluorine atoms, alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, —S-alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, OH, CN, $NO_2$, NR27R28, C(O)R29, C(O)NR30R31, $S(O)_o$R32, $S(O)_p$NR33R34, aryl, heteroaryl, arylalkyl with alkyl having 1, 2, 3 or 4 carbon atoms or heteroarylalkyl with alkyl having 1, 2, 3 or 4 carbon atoms;

R27 is hydrogen or alkyl having 1, 2, 3 or 4 carbon atoms;

R28 is hydrogen, alkyl having 1, 2, 3 or 4 carbon atoms, aryl, C(O)H, C(O)alkyl with alkyl having 1, 2, 3 or 4 carbon atoms or C(O)aryl;

R29 is hydrogen, OH, alkyl with 1, 2, 3 or 4 carbon atoms, alkoxy with 1, 2, 3 or 4 carbon atoms or aryl;

R30, R31, R33 and R34
are, independently of one another, hydrogen, alkyl having 1, 2, 3 or 4 carbon atoms or aryl;

R32 is OH, alkyl having 1, 2, 3 or 4 carbon atoms, alkoxy with 1, 2, 3 or 4 carbon atoms or aryl;

o and p
are, independently of one another, 1 or 2;

R7 is hydrogen, alkyl having 1, 2, 3 or 4 carbon atoms or C(O)R35;

R35 is hydrogen, alkyl with 1, 2, 3 or 4 carbon atoms or aryl;

Y1, Y2, Y3 and Y4
are, independently of one another, —CR8— or nitrogen, with the proviso that at least two of Y1, Y2, Y3 and Y4 are defined as —CR8-;

R8 is hydrogen, F, Cl, Br, I, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 1, 2, 3, 4, 5 or 6 carbon atoms, in which 1, 2, 3, 4, 5, 6, 7, 8, 9, 10, or 11 hydrogen atoms may be substituted by fluorine atoms, alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, —S-alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, OH, CN, $NO_2$, NR36R37, C(O)R38, C(O)NR39R40, $S(O)_q$R41, $S(O)_r$NR42R43, aryl, heteroaryl, arylalkyl with alkyl having 1, 2, 3 or 4 carbon atoms or heteroarylalkyl with alkyl having 1, 2, 3 or 4 carbon atoms;

R36 is hydrogen or alkyl having 1, 2, 3 or 4 carbon atoms

R37 is hydrogen, alkyl having 1, 2, 3 or 4 carbon atoms, aryl, C(O)H, C(O)alkyl with alkyl having 1, 2, 3 or 4 carbon atoms or C(O)aryl;

R38 is hydrogen, OH, alkyl with 1, 2, 3 or 4 carbon atoms, alkoxy with 1, 2, 3 or 4 carbon atoms or aryl;

R39, R40, R42 and R43
are, independently of one another, hydrogen, alkyl having 1, 2, 3 or 4 carbon atoms or aryl;

R41 is OH, alkyl having 1, 2, 3 or 4 carbon atoms, alkoxy with 1, 2, 3 or 4 carbon atoms or aryl;

q and r
are, independently of one another, 1 or 2;

A is cycloalkyl having 3, 4, 5, 6, 7 or 8 carbon atoms, heterocycle, aryl or heteroaryl;

in which the cycloalkyl or heterocycle radical can be condensed to an aryl or heteroaryl radical and in which the cycloalkyl or heterocycle radical and the optionally condensed aryl or heteroaryl radical are unsubstituted or substituted by 1, 2, 3 or 4 radicals selected from the group consisting of F, Cl, Br, I, OH, CN, $NO_2$, $SF_5$, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 1, 2, 3, 4, 5 or 6 carbon atoms, in which 1, 2, 3, 4, 5, 6, 7, 8, 9, 10 or 11 hydrogen atoms may be substituted by fluorine atoms, alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, —S-alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, —NR9R10, C(O)R44, C(O)N45R46, $S(O)_s$R47, $S(O)_t$NR48R49, —$(CH_2)_k$-aryl or —$(CH_2)_l$-heteroaryl, in which the aryl and heteroaryl radicals can be substituted by F, Cl, Br, I, alkoxy having 1, 2, 3 or 4 carbon atoms, alkyl having 1, 2, 3 or 4 carbon atoms or $O_a$—$(CH_2)_b$—$(CF_2)_c$—$CF_3$;

R9 is hydrogen or alkyl having 1, 2, 3 or 4 carbon atoms

R10 is hydrogen, alkyl having 1, 2, 3 or 4 carbon atoms, aryl, C(O)H, C(O)alkyl having 1, 2, 3 or 4 carbon atoms or C(O)aryl;

R44 is hydrogen, OH, alkyl with 1, 2, 3 or 4 carbon atoms, alkoxy with 1, 2, 3 or 4 carbon atoms, cycloalkyl having 3, 4, 5 or 6 carbon atoms or aryl;

R45, R46, R48 and R49
are, independently of one another, hydrogen, alkyl having 1, 2, 3 or 4 carbon atoms or aryl;

R47 is OH, alkyl having 1, 2, 3 or 4 carbon atoms, alkoxy with 1, 2, 3 or 4 carbon atoms or aryl;
a is zero or 1;
b, c, k and l
are, independently of one another, zero, 1, 2 or 3;
s and t
are, independently of one another, 1 or 2;
in which the aryl or heteroaryl radical can be condensed to an cycloalkyl or heterocycle radical and in which the aryl or heteroaryl radical and the optionally condensed cycloalkyl or heterocycle radical are unsubstituted or substituted by 1, 2, 3 or 4 radicals selected from the group consisting of F, Cl, Br, I, OH, CN, NO$_2$, SF5, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 1, 2, 3, 4, 5 or 6 carbon atoms, in which 1, 2, 3, 4, 5, 6, 7, 8, 9, 10 or 11 hydrogen atoms may be substituted by fluorine atoms, alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, —S-alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, —NR9R10, C(O)R44, C(O)N45R46, S(O)$_s$R47, S(O)$_t$NR48R49, —(CH$_2$)$_k$-aryl or —(CH$_2$)$_l$-heteroaryl, in which the aryl and heteroaryl radicals can be substituted by F, Cl, Br, I, alkoxy having 1, 2, 3 or 4 carbon atoms, alkyl having 1, 2, 3 or 4 carbon atoms or O$_a$—(CH$_2$)$_b$—(CF$_2$)C—CF$_3$;
R9 is hydrogen or alkyl having 1, 2, 3 or 4 carbon atoms
R10 is hydrogen, alkyl having 1, 2, 3 or 4 carbon atoms, aryl, C(O)H, C(O)alkyl having 1, 2, 3 or 4 carbon atoms or C(O)aryl;
R44 is hydrogen, OH, alkyl with 1, 2, 3 or 4 carbon atoms, alkoxy with 1, 2, 3 or 4 carbon atoms, cycloalkyl having 3, 4, 5 or 6 carbon atoms or aryl;
R45, R46, R48 and R49
are, independently of one another, hydrogen, alkyl having 1, 2, 3 or 4 carbon atoms or aryl;
R47 is OH, alkyl having 1, 2, 3 or 4 carbon atoms, alkoxy with 1, 2, 3 or 4 carbon atoms or aryl;
a is zero or 1;
b, c, k and l
are, independently of one another, zero, 1, 2 or 3;
s and t
are, independently of one another, 1 or 2;
B is —O—C(R11R12)-, —C(R50R51)—O—, —C☐C—, —CR52=CR53-, —C(R13R14)—C(R5R16)-, —NR17-C(R18R19)-, —C(R54R55)—NR56-, —NR20-C(O)— or —C(O)—NR57-;
R11, R12, R13, R14, R15, R16, R17, R18, R19, R20, R50, R51, R52, R53, R54, R55, R56 and R57
are, independently of one another, hydrogen or alkyl having 1, 2, 3 or 4 carbon atoms, in which 1, 2, 3, 4, 5, 6, 7, 8 or 9 hydrogen atoms may be substituted by fluorine atoms;
R1 is alkyl having 1, 2, 3, 4, 5 or 6 carbon atoms;
which can be unsubstituted or substituted by 1, 2, 3, 4 or 5 radicals selected from the group consisting of F, Cl, Br, I or —O$_i$—(CH$_2$)$_j$—R25;
i is 0 or 1;
j is 0, 1, 2 or 3;
R25 is hydrogen, phenyl, heteroaryl having 5 or 6 atoms, cycloalkyl having 3, 4, 5 or 6 carbon atoms or heterocyclyl having 3, 4 5, 6, 7 or 8 atoms, in which phenyl, heteroaryl, cycloalkyl or heterocyclyl are unsubstituted or substituted by 1, 2 or 3 radicals selected from F, Cl, Br or I,
and
R2 is phenyl, heteroaryl having 5 or 6 atoms, cycloalkyl having 3, 4, 5, 6, 7 or 8 carbon atoms or heterocyclyl having 3, 4 5, 6, 7 or 8 atoms;
wherein phenyl, heteroaryl having 5 or 6 atoms, cycloalkyl having 3, 4, 5, 6, 7 or 8 carbon atoms or heterocyclyl having 3, 4 5, 6, 7 or 8 atoms are unsubstituted or substituted by 1, 2, 3, 4 or 5 radicals selected from the group consisting of F, Cl, Br, I, OH, CN, NO$_2$, SCF$_3$, SF$_5$, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms, cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkoxy having 3, 4, 5 or 6 carbon atoms, in which 1, 2, 3, 4, 5, 6, 7, 8, 9, 10 or 11 hydrogen atoms may be substituted by fluorine atoms or cycloalkylalkoxy having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms;
or alkyl having 1, 2, 3, 4, 5 or 6 carbon atoms; which is substituted by 1, 2, 3, 4 or 5 radicals selected from the group consisting of —O$_m$—(CH$_2$)$_n$—R26;
m is 0 or 1;
n iso, 1, 2 or 3;
R26 is cycloalkyl having 3, 4, 5 or 6 carbon atoms which is unsubstituted or substituted by 1, 2 or 3 radicals selected from F, Cl, Br or I;
or
R1 and R2
form, together with the carbon atom to which they are attached, a 5- or 6-membered partially unsaturated carbon ring containing one or two double bonds; and in which the formed ring can optionally be condensed to phenyl, heteroaryl having 5 or 6 atoms, cycloalkyl having 3, 4, 5, 6, 7 or 8 carbon atoms or heterocyclyl having 3, 4, 5, 6, 7 or 8 atoms;
wherein the formed ring and the optionally condensed phenyl, heteroaryl, cycloalkyl or heterocyclyl radical can be unsubstituted or substituted by 1, 2, 3, 4 or 5 radicals selected from the group consisting of F, Cl, Br, I, CN, NO$_2$, SCF$_3$, SF$_5$, or alkyl having 1, 2, 3 or 4 carbon atoms;
or
R1 and R2
form, together with the carbon atom to which they are attached, a 4-, 5- or 6-membered carbon ring, wherein one carbon atom, which is not adjacent to the carbon atom to which R1 and R2 are attached, is replaced by —O—, —NR58- or —S(O)$_w$—, and in which the formed ring can be saturated or partially unsaturated, and in which the formed ring can optionally be condensed to phenyl, heteroaryl having 5 or 6 atoms, cycloalkyl having 3, 4, 5, 6, 7 or 8 carbon atoms or heterocyclyl having 3, 4, 5, 6, 7 or 8 atoms,
wherein the formed ring and the optionally condensed phenyl, heteroaryl, cycloalkyl or heterocyclyl radical can be unsubstituted or substituted by 1, 2, 3, 4 or 5 radicals selected from the group consisting of F, Cl, Br, I, CN, $NO_2$, $SCF_3$, $SF_5$, or alkyl having 1, 2, 3 or 4 carbon atoms;

R58 is hydrogen, alkyl having 1, 2, 3 or 4 carbon atoms or C(O)R59;

R59 is hydrogen, alkyl with 1, 2, 3 or 4 carbon atoms or phenyl;

w is 0, 1 or 2;

and/or a pharmaceutically acceptable salt and/or a prodrug thereof.

Preference is given to a compound of the formula I, in which:

X is —CR3═CR4-, —CR5═N—, —N═CR6-, —NR7- or —S—;

R3, R4, R5 and R6
are, independently of one another, hydrogen, F, Cl, Br, I, alkyl having 1, 2, 3 or 4 carbon atoms or alkoxy having 1, 2, 3 or 4 carbon atoms;

R7 is hydrogen or alkyl having 1, 2, 3 or 4 carbon atoms;

Y1, Y2, Y3 and Y4
are, independently of one another, —CR8- or nitrogen, with the proviso that at least two of Y1, Y2, Y3 and Y4 are defined as —CR8-;

R8 is hydrogen, F, Cl, Br, I or alkyl having 1, 2, 3 or 4 carbon atoms;

A is cycloalkyl having 3, 4, 5, 6, 7 or 8 carbon atoms, heterocycle, aryl or heteroaryl;

in which the cycloalkyl or heterocycle radical can be condensed to an aryl radical and in which the cycloalkyl or heterocycle radical is unsubstituted or substituted by 1, 2 or 3 radicals selected from the group consisting of F, Cl, Br, I or alkyl having 1, 2, 3 or 4 carbon atoms, —C(O)-alkyl having 1, 2, 3 or 4 carbon atoms, —C(O)-cycloalkyl having 3, 4, 5 or 6 carbon atoms or —C(O)O-alkyl having 1, 2, 3 or 4 carbon atoms;

in which the aryl or heteroaryl radical can be condensed to an cycloalkyl or heterocycle radical and in which the aryl or heteroaryl radical is unsubstituted or substituted by 1, 2, 3 or 4 radicals selected from the group consisting of F, Cl, Br, I, CN, $NO_2$, $SF_5$, —NR9R10, alkoxy having 1, 2, 3 or 4 carbon atoms, alkyl having 1, 2, 3, 4, 5 or 6 carbon atoms, —$O_a$—$(CH_2)_b$—$(CF_2)_c$—$CF_3$, —$O_d$—$CHF_2$, —$O_e$—$CH_2F$, —$SO_f$-alkyl having 1, 2, 3 or 4 carbon atoms, S—$(CH_2)_g$—$(CF_2)_h$—$CF_3$, —$(CH_2)_k$-aryl or —$(CH_2)_l$-heteroaryl, in which the aryl and heteroaryl radicals can be substituted by F, Cl, Br, I, $CF_3$, alkoxy having 1, 2, 3 or 4 carbon atoms or alkyl having 1, 2, 3 or 4 carbon atoms;

R9 and R10
are, independently of one another, hydrogen or alkyl having 1, 2, 3 or 4 carbon atoms;

a, d and e
are, independently of one another, zero or 1;

b, c, g, h, k and l
are, independently of one another, zero, 1, 2 or 3;

f is zero, 1 or 2;

B is —O—(CR11R12)-, —C≡C—, —C(R13R14—C(R15R16)-, —NR17-C(R18R19)- or —NR20-C(O)-;

R11, R12, R13, R14, R15, R16, R17, R18, R19 and R20
are, independently of one another, hydrogen or alkyl having 1, 2, 3 or 4 carbon atoms;

R1 is alkyl having 1, 2, 3, 4, 5 or 6 carbon atoms;
which can be unsubstituted or substituted by 1, 2, 3, 4 or 5 radicals selected from the group consisting of F, Cl, Br, I or —$O_i$—$(CH_2)_j$—R25;

i is 0 or 1;

j is 0, 1, 2 or 3;

R25 is hydrogen, phenyl, heteroaryl having 5 or 6 atoms, cycloalkyl having 3, 4, 5 or 6 carbon atoms or heterocyclyl having 3, 4 5, 6, 7 or 8 atoms, in which the phenyl, heteroaryl, cycloalkyl or heterocyclyl are unsubstituted or substituted by 1, 2 or 3 radicals selected from F, Cl, Br or I;

and

R2 is phenyl, heteroaryl having 5 or 6 atoms, cycloalkyl having 3, 4, 5, 6, 7 or 8 carbon atoms or heterocyclyl having 3, 4 5, 6, 7 or 8 atoms;

wherein phenyl, heteroaryl having 5 or 6 atoms, cycloalkyl having 3, 4, 5, 6, 7 or 8 carbon atoms or heterocyclyl having 3, 4 5, 6, 7 or 8 atoms are unsubstituted or substituted by 1, 2, 3, 4 or 5 radicals selected from the group consisting of F, Cl, Br, I, OH, CN, $NO_2$, $SCF_3$, $SF_5$, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms;

or alkyl having 1, 2, 3, 4, 5 or 6 carbon atoms,
which is substituted by —$O_m$—$(CH_2)_n$—R26;

m is 0 or 1;

n is 0, 1, 2 or 3;

R26 is cycloalkyl having 3, 4, 5 or 6 carbon atoms which is unsubstituted or substituted by 1, 2 or 3 radicals selected from F, Cl, Br or I;

or

R1 and R2
form, together with the carbon atom to which they are attached, a 5- or 6-membered partially unsaturated carbon ring containing one or two double bonds and in which the formed ring can optionally be condensed to phenyl, wherein the formed ring and the optionally condensed phenyl, can be unsubstituted or substituted by 1, 2, 3, 4 or 5 radicals selected from the group consisting of F, Cl, Br, I, CN, $NO_2$, $SCF_3$, $SF_5$, or alkyl having 1, 2, 3 or 4 carbon atoms;

or

R1 and R2
form, together with the carbon atom to which they are attached, a 4-, 5- or 6-membered carbon ring, wherein one carbon atom, which is not adjacent to the carbon atom to which R1 and R2 are attached, is replaced by —O—, —NR58- or —$S(O)_w$—, and in which the formed ring can be saturated or partially unsaturated, and in which the formed ring can optionally be condensed to phenyl, wherein the formed ring and the optionally condensed phenyl, can be unsubstituted or substituted by 1, 2, 3, 4 or 5 radicals selected from the group consisting of F, Cl, Br, I, CN, $NO_2$, $SCF_3$, $SF_5$, or alkyl having 1, 2, 3 or 4 carbon atoms;

R58 is hydrogen, alkyl having 1, 2, 3 or 4 carbon atoms or C(O)R59;

R59 is hydrogen, alkyl with 1, 2, 3 or 4 carbon atoms or phenyl;

w is 0, 1 or 2;

and/or a pharmaceutically acceptable salt and/or prodrug thereof.

Particular preference is given to a compound of the formula I in which:

X is —CR3=CR4-, —CR5=N—, —N=CR6-, —NH— or —S—;

R3, R4, R5 and R6
are, independently of one another, hydrogen, F, Cl or Br;

Y1, Y2, Y3 and Y4
are, independently of one another, —CR8- or nitrogen, with the proviso that at least three of Y1, Y2, Y3 and Y4 are defined as —CR8-;

R8 is hydrogen, F or Cl;

A is cyclohexyl or an aryl or heteroaryl radical selected from phenyl, naphthyl, indanyl, thienyl, pyridyl, oxazolyl, isoxazolyl, thiazolyl, imidazolyl, pyrazolyl, pyrazinyl, pyrimidinyl, pyridazinyl, oxadiazolyl, triazolyl, benzothiophenyl, benzoxazolyl, benzothiazolyl or quinolyl;

in which the cyclohexyl is unsubstituted or substituted by 1, 2 or 3 radicals selected from the group consisting of F or alkyl having 1, 2, 3 or 4 carbon atoms;

in which the aryl or heteroaryl radical is unsubstituted or substituted by 1, 2 or 3 radicals selected from the group consisting of F, Cl, Br, CN, $NO_2$, $SF_5$, —$N(CH_3)_2$, methoxy, ethoxy, alkyl having 1, 2, 3 or 4 carbon atoms, —$CF_3$, —$OCF_3$, —$OCH_2CF_3$, —$OCHF_2$, —$SCH_3$—, —$SOCH_3$, —$SO_2CH_3$, —$SCF_3$, phenyl or benzyl; wherein phenyl can be substituted by Cl;

B is —O—C(R11R12)-; —C≡C—, —C(R13R14)—C(R15R16)-, —NR17-C(R18R19)- or —NR20-C(O)-;

R11, R13, R14, R15, R16, R18 and R19
are hydrogen;

R12, R17 and R20
are hydrogen or methyl;

R1 is alkyl having 1, 2, 3, 4, 5 or 6 carbon atoms
and

R2 is phenyl, heteroaryl having 5 or 6 atoms, cycloalkyl having 3, 4, 5, 6, 7 or 8 carbon atoms or heterocyclyl having 3, 4, 5, 6, 7 or 8 atoms;

wherein phenyl, heteroaryl having 5 or 6 atoms, cycloalkyl having 3, 4, 5, 6, 7 or 8 carbon atoms or heterocyclyl having 3, 4, 5, 6, 7 or 8 atoms are unsubstituted or substituted by 1, 2 or 3 radicals selected from the group consisting of F, Cl, Br, I or alkyl having 1, 2, 3 or 4 carbon atoms;

or alkyl having 1, 2, 3, 4, 5 or 6 carbon atoms;

which is substituted by —$O_m$—$(CH_2)_n$—R26;

m is 0 or 1;
n is 0, 1, 2 or 3;
R26 is cycloalkyl having 3, 4, 5 or 6 carbon atoms which is unsubstituted or substituted by 1, 2 or 3 radicals selected from F, Cl, Br or I;

or
R1 and R2
form, together with the carbon atom to which they are attached, a 5- or 6-membered partially unsaturated carbon ring containing one or two double bonds, wherein the formed ring can be unsubstituted or substituted by 1, 2, 3, 4 or 5 radicals selected from the group consisting of F, Cl, Br, I, CN, $NO_2$, $SCF_3$, $SF_5$, or alkyl having 1, 2, 3 or 4 carbon atoms;

or
R1 and R2
form, together with the carbon atom to which they are attached, a 4-, 5- or 6-membered carbon ring, wherein one carbon atom, which is not adjacent to the carbon atom to which R1 and R2 are attached, is replaced by —O—, —NR58- or —$S(O)_w$—, and in which the formed ring can be saturated or partially unsaturated, wherein the formed ring can be unsubstituted or substituted by 1, 2, 3, 4 or 5 radicals selected from the group consisting of F, Cl, Br, I, CN, $NO_2$, $SCF_3$, $SF_5$, or alkyl having 1, 2, 3 or 4 carbon atoms;

R58 is hydrogen, alkyl having 1, 2, 3 or 4 carbon atoms or C(O)R59;

R59 is hydrogen, alkyl with 1, 2, 3 or 4 carbon atoms or phenyl;

w is 0, 1 or 2;

and/or a pharmaceutically acceptable salt and/or prodrug thereof.

Special preference is given to a compound of the formula I, in which

X is —CR3=CR4- or —S—;

R3 and R4
are, independently of one another, hydrogen, F, Cl or Br;

Y1, Y2, Y3 and Y4
are, independently of one another, —CR8-;

R8 is hydrogen, F or Cl;

A is cyclohexyl or an aryl or heteroaryl radical selected from phenyl, naphthyl, indanyl, thienyl, pyridyl, thiazolyl, pyrazinyl, pyrimidinyl, pyridazinyl, benzothiophenyl, benzothiazolyl or quinolyl, wherein cyclohexyl is unsubstituted or substituted by 1, 2 or 3 radicals selected from the group consisting of F or alkyl having 1, 2, 3 or 4 carbon atoms, and wherein the aryl or heteroaryl radical is unsubstituted or substituted by 1, 2 or 3 radicals selected from the group consisting of F, Cl, Br, $SF_5$, methoxy, ethoxy, alkyl having 1, 2, 3 or 4 carbon atoms, $CF_3$, $OCF_3$, $OCH_2CF_3$, $OCHF_2$, $SCH_3$, $SCF_3$ and phenyl;

B is —O—C(R11R12)-;

R11 is hydrogen;

R12 is hydrogen or methyl;

R1 is alkyl having 1, 2, 3 or 4 carbon atoms
and

R2 is phenyl,
which is unsubstituted or substituted by 1, 2 or 3 radicals selected from the group consisting of F, Cl, Br, I or alkyl having 1, 2, 3 or 4 carbon atoms;

or methyl or ethyl which is substituted by —$O_m$—$(CH_2)_n$—R26;

m is 0 or 1;
n is 0, 1, 2 or 3;
R26 is cycloalkyl having 3, 4, 5 or 6 carbon atoms;

or
R1 and R2
form, together with the carbon atom to which they are attached, a 5- or 6-membered partially unsaturated carbon ring containing one or two double bonds;

or
R1 and R2
form, together with the carbon atom to which they are attached, a 4-, 5- or 6-membered carbon ring, wherein one carbon atom, which is not adjacent to the carbon atom to which R1 and R2 are attached, is replaced by —O—, —NH— or —S—, and in which the formed ring can be saturated or partially unsaturated;

and/or a pharmaceutically acceptable salt and/or prodrug thereof.

Special preference is given to a compound of the formula I, in which

X is —CR3=CR4

—R3 and R4 are, independently of one another, hydrogen or F;
Y1, Y2, Y3 and Y4 are —CH—;
A is phenyl, pyridyl, benzothiazolyl,
   which is unsubstituted or substituted by —CF$_3$, —OCF$_3$, or —SCF$_3$;
B is —O—CH$_2$—;
R1 is methyl or ethyl
and
R2 is phenyl;
or
R1 and R2
   form, together with the carbon atom to which they are attached, a cyclopentene ring;
or
R1 and R2
   form, together with the carbon atom, to which they are attached, a tetrahydrothiophene, a tetrahydrothiopyrane, a tetrahydropyrane or a tetrahydrofurane ring; preferably a tetrahydrothiophene, a tetrahydrothiopyrane, or a tetrahydropyrane ring;
and/or a pharmaceutically acceptable salt and/or a prodrug thereof.

In one embodiment X in compounds of formula I is described by —CR3═CR4-, —CR5═N—, —N═CR6-, —NR7- or —S—, wherein R3, R4, R5 and R6 are independently of one another, hydrogen, F, Cl, Br, I, alkyl having 1, 2, 3 or 4 carbon atoms or alkoxy having 1, 2, 3 or 4 carbon atoms, and R7 is hydrogen or alkyl having 1, 2, 3 or 4 carbon atoms, preferably hydrogen; preference is given to compounds, in which X is described by —CR3═CR4-, —CR5═N—, —N═CR6-, —NH— or —S—, wherein R3, R4, R5 and R6 are, independently of one another, hydrogen, F, Cl, Br, I or alkyl having 1, 2, 3 or 4 carbon atoms, preferably R3, R4, R5 and R6 are, independently of one another, hydrogen, F, Cl or Br;
particular preference is given to compounds, in which X is described as —CR3═CH—, —CH═N—, —N═CH, NH or —S—, wherein R3 is defined as hydrogen, F, Cl or Br; more particular preference is given to compounds, in which X is described as —CR3═CH— or —S—, wherein R3 is defined as hydrogen, F, Cl or Br; most particular preference is given to compounds, in which X is described —CR3═CH—, wherein R3 is defined as hydrogen or F;

Linker X is attached with its left hand side to the carbon atom in the six-membered ring and with its right hand side to the other carbon atom.

In a further embodiment Y1, Y2, Y3 and Y4 in compounds of formula I are, independently of one another, described by —CR8- or Nitrogen, with the proviso that at least two of Y1, Y2, Y3 and Y4 are defined as —CR8-, wherein R8 is hydrogen, F, Cl, Br, I or alkyl having 1, 2, 3 or 4 carbon atoms; preferably at least three of Y1, Y2, Y3 and Y4 are defined as —CR8, wherein R8 is hydrogen, F, Cl, Br, I or alkyl having 1, 2, 3 or 4 carbon atoms, preferably hydrogen or Cl, for example hydrogen; for example Y1, Y2 and Y3 are CH and Y4 is N or Y1, Y2, Y3 and Y4 are CR8, wherein R8 is hydrogen, F or Cl, in particular hydrogen.

In a further embodiment A in compounds of formula I is described by cycloalkyl having 3, 4, 5, 6, 7 or 8 carbon atoms, heterocycle, aryl or heteroaryl, wherein the cycloalkyl or heterocycle radical can be condensed to an aryl radical and wherein the cycloalkyl or heterocycle radical is unsubstituted or substituted by 1, 2 or 3 radicals selected from the group consisting of F, Cl, Br, I, alkyl having 1, 2, 3 or 4 carbon atoms, —C(O)-alkyl having 1, 2, 3 or 4 carbon atoms, —C(O)-cycloalkyl having 3, 4, 5 or 6 carbon atoms or —C(O)O-alkyl having 1, 2, 3 or 4 carbon atoms and wherein the aryl or heteroaryl radical can be condensed to an cycloalkyl or heterocycle radical and wherein the aryl or heteroaryl radical is unsubstituted or substituted by 1, 2, 3 or 4 radicals selected from the group consisting of F, Cl, Br, I, CN, NO$_2$, SF$_5$, —NR9R10, alkoxy having 1, 2, 3 or 4 carbon atoms, alkyl having 1, 2, 3, 4, 5 or 6 carbon atoms, —O$_a$—(CH$_2$)$_b$—(CF$_2$)$_c$— CF$_3$, —O$_d$—CHF2, —O$_e$—CH$_2$F, —SO$_f$-alkyl having 1, 2, 3 or 4 carbon atoms, S—(CH$_2$)$_g$—(CF$_2$)$_h$—CF$_3$, —(CH$_2$)$_k$-aryl or —(CH$_2$)$_l$-heteroaryl, in which the aryl and heteroaryl radicals can be substituted by F, Cl, Br, I, alkoxy having 1, 2, 3 or 4 carbon atoms or alkyl having 1, 2, 3 or 4 carbon atoms, wherein R9 and R10 are, independently of one another, hydrogen or alkyl having 1, 2, 3 or 4 carbon atoms, a, d and e are, independently of one another, zero or 1, b, c, g, h, k and l are, independently of one another, zero, 1, 2 or 3 and f is zero, 1 or 2.

Preference is given to compounds, wherein A is described by cyclohexyl, phenyl, naphthyl, indanyl, thienyl, pyridyl, oxazolyl, isoxazolyl, thiazolyl, imidazolyl, pyrazolyl, pyrazinyl, pyrimidinyl, pyridazinyl, oxadiazolyl, triazolyl, benzothiophenyl, benzoxazolyl, benzothiazolyl or quinolyl, wherein cyclohexyl is unsubstituted or substituted by 1, 2 or 3 radicals selected from the group consisting of F or alkyl having 1, 2, 3 or 4 carbon atoms, in particular methyl, and wherein the aryl or heteroaryl radical is unsubstituted or substituted by 1, 2 or 3 radicals selected from the group consisting of F, Cl, Br, CN, NO$_2$, SF$_5$, —N(CH$_3$)$_2$, methoxy, ethoxy, alkyl having 1, 2, 3 or 4 carbon atoms, CF$_3$, OCF$_3$, OCH$_2$CF$_3$, OCHF$_2$, SCH$_3$, SOCH$_3$, SO$_2$CH$_3$, SCF$_3$, phenyl or benzyl, wherein phenyl can be substituted by Cl.

Particular preference is given to compounds of formula I, in which A is described by:

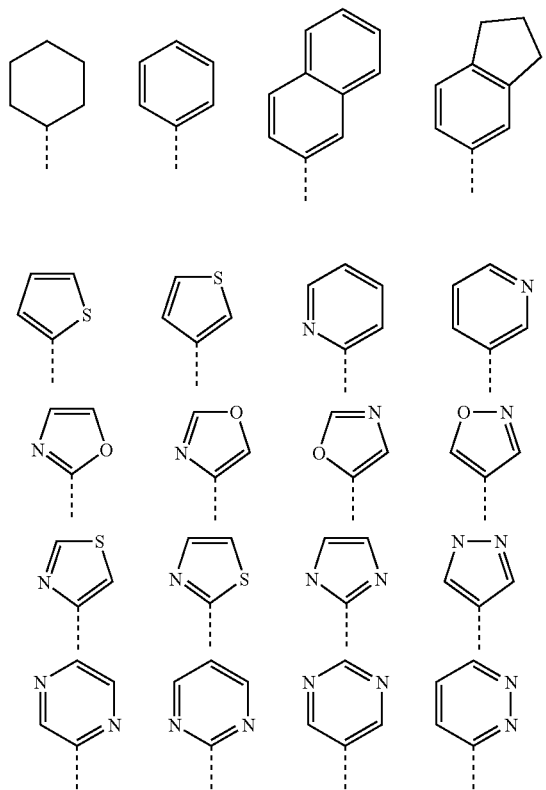

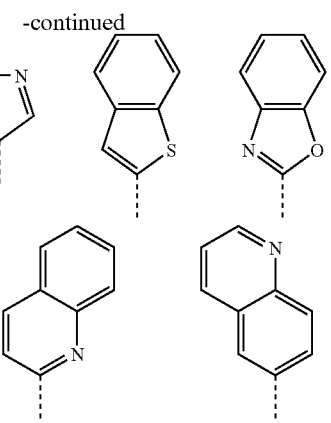

wherein, cyclohexyl is unsubstituted or substituted by 1, 2 or 3 radicals selected from the group consisting of F or alkyl having 1, 2, 3 or 4 carbon atoms, in particular methyl, and wherein the aryl or heteroaryl radical is unsubstituted or substituted by 1, 2 or 3 radicals selected from the group consisting of F, Cl, Br, CN, $NO_2$, $SF_5$, —$N(CH_3)_2$, methoxy, ethoxy, alkyl having 1, 2, 3 or 4 carbon atoms, $CF_3$, $OCF_3$, $OCH_2CF_3$, $OCHF_2$, $SCH_3$, $SOCH_3$, $SO_2CH_3$, $SCF_3$, phenyl and benzyl, wherein phenyl can be substituted by Cl. The broken line (---) indicates where the substituent A is attached to B.

Also particular preference is given to compounds, wherein A is described as cyclohexyl or an aryl or heteroaryl radical selected from phenyl, naphthyl, indanyl, thienyl, pyridyl, thiazolyl, pyrazinyl, pyrimidinyl, pyridazinyl, benzothiophenyl, benzothiazolyl or quinolyl, wherein cyclohexyl is unsubstituted or substituted by 1, 2 or 3 radicals selected from the group consisting of F or alkyl having 1, 2, 3 or 4 carbon atoms, in particular methyl, and wherein the aryl or heteroaryl radical is unsubstituted or substituted by 1, 2 or 3 radicals selected from the group consisting of F, Cl, Br, $SF_5$, methoxy, ethoxy, alkyl having 1, 2, 3 or 4 carbon atoms, $CF_3$, $OCF_3$, $OCH_2CF_3$, $OCHF_2$, $SCH_3$, $SCF_3$ and phenyl;

more particular preference is given to compounds of formula I, in which A is described by phenyl, pyridyl or benzothiazolyl; which are unsubstituted or substituted by 1, 2 or 3 radicals selected from the group consisting of F, Cl, Br, alkyl having 1, 2, 3 or 4 carbon atoms, $CF_3$, $OCF_3$ and $SCF_3$;

most particular prefernce is given to compounds, in which A is described by phenyl, pyridyl or benzothiazolyl, which are unsubstituted or substituted by $CF_3$, $OCF_3$ or $SCF_3$; preferably phenyl is stubstituted by $CF_3$, $OCF_3$ or $SCF_3$, pyridyl is substituted by $CF_3$ and benzothiazolyl is unsubstituted.

In another embodiment A in compounds of formula I is described by unsubstituted cycloalkyl having 3, 4, 5, 6, 7 or 8 carbon atoms, heterocycle, aryl or heteroaryl, in which the cycloalkyl or heterocycle radical can be condensed to an aryl radical and in which the aryl or heteroaryl radical can be condensed to an cycloalkyl or heterocycle radical.

In another embodiment A in compounds of formula I is described by cycloalkyl having 3, 4, 5, 6, 7 or 8 carbon atoms, heterocycle, aryl or heteroaryl, wherein the cycloalkyl or heterocycle radical can be condensed to an aryl radical and wherein the cycloalkyl or heterocycle radical is substituted by 1, 2 or 3 radicals and wherein the aryl or heteroaryl radical can be condensed to an cycloalkyl or heterocycle radical and wherein the aryl or heteroaryl radical is unsubstituted or substituted by 1, 2, 3 or 4 radicals; preference is given to compounds of the formula I in which A is described by a monocyclic ring compound, for example a monocyclic cycloalkyl having 3, 4, 5, 6, 7 or 8 carbon atoms, heterocycle, aryl or heteroaryl, which is at least substituted once in a position not near to the binding site of the cycloalkyl, heterocycle, aryl or heteroaryl to the linker B, for example phenyl or cyclohexyl radicals are at least substituted in position 4 and are optionally additionally substituted by additional radicals; preference is further given to compounds of the formula I in which A is described by a bicyclic ring compound, for example a bicyclic aryl, a bicyclic heteroaryl, a cycloalkyl or heterocycle radical to which an aryl or heteroaryl radical is condensed or an aryl or heteroaryl radical to which an cycloalkyl or heterocycle is condensed, where this bicyclic ring compound is unsubstituted or substituted with small substituents, in particular with F, Cl, $CF_3$, CN or methoxy, preferably in a position not near the binding site of the cycloalkyl, heterocycle, aryl or heteroaryl to the linker B, for example in 2-benzthiazolyl radicals in position 6 and/or 7 and in 2-naphthalene radicals in position 6.

In a further embodiment B in compounds of formula I is described as —O—C(R11R12)-, —C≡C—, —C(R13R14)—C(R15R16)-, —NR17-C(R18R19)- or —NR20-C(O)—, wherein R11, R12, R13, R14, R15, R16, R17, R18, R19 and R20 are, independently of one another, hydrogen or alkyl having 1, 2, 3 or 4 carbon atoms; preference is given to compounds, wherein B is —O—(CR11R12)-, —C≡C— or —CR13R14CR15R16-, wherein R11, R12, R13, R14, R15 and R16 are, independently of one another, hydrogen or alkyl having 1, 2, 3 or 4 carbon atoms, preferably when R11, R13, R14, R15 and R16 are hydrogen and R12 is hydrogen or alkyl having 1, 2, 3 or 4 carbon atoms, for example methyl; more preference is given to compounds, wherein B is —O—(CR11R12)-, preferably when R11 is hydrogen and R12 is hydrogen or alkyl having 1, 2, 3 or 4 carbon atoms, for example methyl.

Linker B is attached with its left hand side to the ring system and with its right hand side to the residue A.

In a further embodiment of compounds of formula I R1 is alkyl having 1, 2, 3, 4, 5 or 6 carbon atoms;
  which can be unsubstituted or substituted by 1, 2, 3, 4 or 5 radicals selected from the group consisting of F, Cl, Br, I or —$O_i$—$(CH_2)_j$—R25;
  i is 0 or 1;
  j is 0, 1, 2 or 3;
  R25 is hydrogen, phenyl, heteroaryl having 5 or 6 atoms, cycloalkyl having 3, 4, 5 or 6 carbon atoms or heterocyclyl having 3, 4 5, 6, 7 or 8 atoms, in which the phenyl, heteroaryl, cycloalkyl or heterocyclyl are unsubstituted or substituted by 1, 2 or 3 radicals selected from F, Cl, Br or I,
and
R2 is phenyl, heteroaryl having 5 or 6 atoms, cycloalkyl having 3, 4, 5, 6, 7 or 8 carbon atoms or heterocyclyl having 3, 4 5, 6, 7 or 8 atoms;
  wherein phenyl, heteroaryl having 5 or 6 atoms, cycloalkyl having 3, 4, 5, 6, 7 or 8 carbon atoms or heterocyclyl having 3, 4 5, 6, 7 or 8 atoms are unsubstituted or substituted by 1, 2, 3, 4 or 5 radicals selected from the group consisting of F, Cl, Br, I, OH, CN, $NO_2$, $SCF_3$, $SF_5$, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms;
or alkyl having 1, 2, 3, 4, 5 or 6 carbon atoms,
  which is substituted by —$O_m$—$(CH_2)_n$—R26;
  m is 0 or 1;
  n is 0, 1, 2 or 3;

R26 is cycloalkyl having 3, 4, 5 or 6 carbon atoms which is unsubstituted or substituted by 1, 2 or 3 radicals selected from F, Cl, Br or I;
preferably, R2 is phenyl, heteroaryl having 5 or 6 atoms, cycloalkyl having 3, 4, 5, 6, 7 or 8 carbon atoms or heterocyclyl having 3, 4 5, 6, 7 or 8 atoms;
wherein phenyl, heteroaryl having 5 or 6 atoms, cycloalkyl having 3, 4, 5, 6, 7 or 8 carbon atoms or heterocyclyl having 3, 4 5, 6, 7 or 8 atoms are unsubstituted or substituted by 1, 2, 3, 4 or 5 radicals selected from the group consisting of F, Cl, Br, I, OH, CN, $NO_2$, $SCF_3$, $SF_5$, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms
or, in another embodiment,
R1 and R2
    form, together with the carbon atom to which they are attached, a 5- or 6-membered partially unsaturated carbon ring containing one or two double bonds and in which the formed ring can optionally be condensed to phenyl,
        wherein the formed ring and the optionally condensed phenyl, can be unsubstituted or substituted by 1, 2, 3, 4 or 5 radicals selected from the group consisting of F, Cl, Br, I, CN, $NO_2$, $SCF_3$, $SF_5$, or alkyl having 1, 2, 3 or 4 carbon atoms; preferably the formed ring is not condensed;
or, in another embodiment,
R1 and R2
    form, together with the carbon atom to which they are attached, a 4-, 5- or 6-membered carbon ring, wherein one carbon atom, which is not adjacent to the carbon atom to which R1 and R2 are attached, is replaced by —O—, —NR58- or —S(O)$_w$—, and in which the formed ring can be saturated or partially unsaturated, and in which the formed ring can optionally be condensed to phenyl,
        wherein the formed ring and the optionally condensed phenyl, can be unsubstituted or substituted by 1, 2, 3, 4 or 5 radicals selected from the group consisting of F, Cl, Br, I, CN, $NO_2$, $SCF_3$, $SF_5$, or alkyl having 1, 2, 3 or 4 carbon atoms; preferably, the formed ring is not condensed;
    R58 is hydrogen, alkyl having 1, 2, 3 or 4 carbon atoms or C(O)R59;
        R59 is hydrogen, alkyl with 1, 2, 3 or 4 carbon atoms or phenyl;
        preferably, R58 is hydrogen or alkyl having 1, 2, 3 or 4 carbon atoms;
    w is 0, 1 or 2, preferably, w is 0;
In a preferred embodiment of compounds of formula I
R1 is alkyl having 1, 2, 3, 4, 5 or 6 carbon atoms,
and
R2 is phenyl, heteroaryl having 5 or 6 atoms, cycloalkyl having 3, 4, 5, 6, 7 or 8 carbon atoms or heterocyclyl having 3, 4 5, 6, 7 or 8 atoms;
    wherein phenyl, heteroaryl having 5 or 6 atoms, cycloalkyl having 3, 4, 5, 6, 7 or 8 carbon atoms or heterocyclyl having 3, 4 5, 6, 7 or 8 atoms are unsubstituted or substituted by 1, 2 or 3 radicals selected from the group consisting of F, Cl, Br, I or alkyl having 1, 2, 3 or 4 carbon atoms;
    or alkyl having 1, 2, 3, 4, 5 or 6 carbon atoms; which is substituted by —O$_m$—(CH$_2$)$_n$—R26;
        m is 0 or 1;
        n is 0, 1, 2 or 3;
    R26 is cycloalkyl having 3, 4, 5 or 6 carbon atoms which is unsubstituted or substituted by 1, 2 or 3 radicals selected from F, Cl, Br or I;
    preferably, R2 is phenyl, heteroaryl having 5 or 6 atoms, cycloalkyl having 3, 4, 5, 6, 7 or 8 carbon atoms or heterocyclyl having 3, 4 5, 6, 7 or 8 atoms; wherein phenyl, heteroaryl having 5 or 6 atoms, cycloalkyl having 3, 4, 5, 6, 7 or 8 carbon atoms or heterocyclyl having 3, 4 5, 6, 7 or 8 atoms are unsubstituted or substituted by 1, 2 or 3 radicals selected from the group consisting of F, Cl, Br, I or alkyl having 1, 2, 3 or 4 carbon atoms;
or, in another embodiment,
R1 and R2
    form, together with the carbon atom to which they are attached, a 5- or 6-membered partially unsaturated carbon ring containing one or two double bonds,
        wherein the formed ring can be unsubstituted or substituted by 1, 2, 3, 4 or 5 radicals selected from the group consisting of F, Cl, Br, I, CN, $NO_2$, $SCF_3$, $SF_5$, or alkyl having 1, 2, 3 or 4 carbon atoms;
or, in another embodiment,
R1 and R2
    form, together with the carbon atom to which they are attached, a 4-, 5- or 6-membered carbon ring, wherein one carbon atom, which is not adjacent to the carbon atom to which R1 and R2 are attached, is replaced by —O—, —NR58- or —S(O)$_w$—, and in which the formed ring can be saturated or partially unsaturated,
        wherein the formed ring can be unsubstituted or substituted by 1, 2, 3, 4 or 5 radicals selected from the group consisting of F, Cl, Br, I, CN, $NO_2$, $SCF_3$, $SF_5$, or alkyl having 1, 2, 3 or 4 carbon atoms;
    R58 is hydrogen, alkyl having 1, 2, 3 or 4 carbon atoms or C(O)R59;
    R59 is hydrogen, alkyl with 1, 2, 3 or 4 carbon atoms or phenyl;
    preferably, R58 is hydrogen or alkyl having 1, 2, 3 or 4 carbon atoms;
    w is 0, 1 or 2, preferably, w is 0.
In more preferred embodiment of compounds of formula I
R1 is alkyl having 1, 2, 3 or 4 carbon atoms; preferably methyl or ethyl;
and
R2 is phenyl,
    which is unsubstituted or substituted by 1, 2 or 3 radicals selected from the group consisting of F, Cl, Br, I or alkyl having 1, 2, 3 or 4 carbon atoms;
    or is methyl or ethyl, which is substituted by —O$_m$—(CH$_2$)$_n$—R26;
    m is 0 or 1;
    n is 0, 1, 2 or 3; preferably n is 0 or 1;
R26 is cycloalkyl having 3, 4, 5 or 6 carbon atoms;
    preferably, R2 is phenyl, which is unsubstituted or substituted by 1, 2 or 3 radicals selected from of F, Cl, Br, I or alkyl having 1, 2, 3 or 4 carbon atoms;
or, in another embodiment,
R1 and R2
    form, together with the carbon atom to which they are attached, a 5- or 6-membered partially unsaturated carbon ring containing one or two double bonds; preferably the formed ring contains one double bond;
or, in another embodiment,
R1 and R2
    form, together with the carbon atom to which they are attached, a 4-, 5- or 6-membered carbon ring, wherein one carbon atom, which is not adjacent to the carbon atom to which R1 and R2 are attached, is replaced by —O—, —NH— or —S—, and in which the formed ring can be saturated or partially unsaturated; preferably the formed ring is saturated and the carbon atom is replaced by —O— or —S—.

In a most preferred embodiment of compounds of formula I

R1 is methyl or ethyl; preferably ethyl;
and
R2 is phenyl;
or, in another embodiment,
R1 and R2
  form, together with the carbon atom to which they are attached, a cyclopentene ring; preferably a cyclopent-3-ene ring;
or, in another embodiment,
R1 and R2
  form, together with the carbon atom, to which they are attached, a tetrahydrothiophene, a tetrahydrothiopyrane or a tetrahydroppyrane ring; preferably a 3-tetrahydrothiophene, a 4-tetrahydrothiopyrane or a 4-tetrahydropyrane ring.

In given embodiments of the present invention one or more or all of the groups contained in the compounds of formula I can independently of each other have any of the given, preferred, more preferred or most preferred definitions of the groups specified above or any one or some of the specific denotations which are comprised by the definitions of the groups and specified above, all combinations of given or preferred definitions, more preferred or most preferred and/or specific denotations being a subject of the present invention.

Special preference is given to a compound of formula I, selected from the group consisting of:
4-{[1-(4-Trifluoromethyl-benzyloxy)-naphthalene-2-carbonyl]-amino}-tetrahydro-thiopyran-4-carboxylic acid,
1-{[1-(4-Trifluoromethyl-benzyloxy)-naphthalene-2-carbonyl]-amino}-cyclopent-3-enecarboxylic acid,
3-{[1-(Benzothiazol-2-ylmethoxy)-naphthalene-2-carbonyl]-amino}-tetrahydro-thiophene-3-carboxylic acid,
3-{[1-(6-Trifluoromethyl-pyridin-3-ylmethoxy)-naphthalene-2-carbonyl]-amino}-tetrahydro-thiophene-3-carboxylic acid,
4-{[1-(Benzothiazol-2-ylmethoxy)-naphthalene-2-carbonyl]-amino}-tetrahydro-thiopyran-4-carboxylic acid,
4-{[1-(Benzothiazol-2-ylmethoxy)-4-fluoro-naphthalene-2-carbonyl]-amino}-tetrahydro-pyran-4-carboxylic acid,
4-{[4-Fluoro-1-(4-trifluoromethyl-benzyloxy)-naphthalene-2-carbonyl]-amino}-tetrahydro-pyran-4-carboxylic acid,
3-{[1-(4-Trifluoromethoxy-benzyloxy)-naphthalene-2-carbonyl]-amino}-tetrahydro-thiophene-3-carboxylic acid,
2-{[1-(Benzothiazol-2-ylmethoxy)-naphthalene-2-carbonyl]-amino}-2-phenyl-butyric acid,
2-Phenyl-2-{[1-(4-trifluoromethyl-benzyloxy)-naphthalene-2-carbonyl]-amino}-butyric acid,
4-{[1-(4-Trifluoromethylsulfanyl-benzyloxy)-naphthalene-2-carbonyl]-amino}-tetrahydro-thiopyran-4-carboxylic acid or
4-{[4-Fluoro-1-(4-trifluoromethylsulfanyl-benzyloxy)-naphthalene-2-carbonyl]-amino}-tetrahydro-pyran-4-carboxylic acid,
3-{[1-(4-Trifluoromethyl-benzyloxy)-naphthalene-2-carbonyl]-amino}-tetrahydro-furan-3-carboxylic acid,
3-{[4-Chloro-1-(4-trifluoromethyl-benzyloxy)-naphthalene-2-carbonyl]-amino}-tetrahydro-furan-3-carboxylic acid
and/or a pharmaceutically acceptable salt and/or a prodrug thereof.

The compounds of the formula I can be present in the form of their salts. An overview of pharmaceutically employed salts can be found in the "Handbook of Pharmaceutical Salts", edited by P. Heinrich Stahl, Camille G. Wermuth, Verlag Helvetica Chimica Acta, Switzerland, 2002. Suitable base addition salts are salts of all pharmacologically acceptable bases, for example alkali metal, earth alkali metal or metal salts, preferably sodium, potassium, magnesium, calcium or zink salts, or as ammonium salts, for example as salts with ammonia or organic amines or amino acids, preferably as salts formed with ammonia, arginine, benethamine, benzathine, choline, deanol, diethanolamine, diethylamine, 2-(diethylamino)-ethanol, ethanolamine, ethylendiamine, N-methyl-glucamine, hydrabamine, 1H-imidazole, lysine, 4-(2-hydroxyethyl)-morpholine, piperazine, 1-(2-hydroxyethyl)-pyrrolidine, triethanolamine or tromethamine; If the compounds contain a basic group, they are capable of forming salts with acid, for example halides, in particular hydrochlorides, hydrobromides, lactates, sulfates, citrates, tartrates, acetates, phosphates, methylsulfonates, benzenesulfonates, p-toluenesulfonates, adipinates, fumarates, gluconates, glutamates, glycerolphosphates, maleates, benzoates, oxalates and pamoates. This group also corresponds to the physiologically acceptable anions; but also trifluoroacetates. They can also be present as zwitterions.

If the compounds of the present invention contain one or more centers of asymmetry, these may independently of one another have the S and the R configuration. The compounds may be in the form of optical isomers, of diastereomers, of racemates or of mixtures thereof in any ratio.

The compounds of the formula I according to the invention can contain mobile hydrogen atoms, that is be present in various tautomeric forms. The present invention relates to all the tautomers of the compounds of the formula I.

The present invention furthermore encompasses derivatives of compounds of the formula I, for example solvates, such as hydrates and adducts with alcohols, esters, prodrugs and other physiologically tolerated derivatives of compounds of the formula I, and also active metabolites of compounds of the formula I. Further the invention contains all crystal modifications of compounds of formula I.

The invention relates, in particular, to prodrugs of the compounds of the formula I which are not necessarily pharmacologically active in vitro but which are converted in vivo, under physiological conditions, into active compounds of the formula I, for example by hydrolysis in blood. The skilled person is familiar with suitable prodrugs for the compounds of the formula I, that is chemically modified derivatives of the compounds of the formula I possessing properties which have been improved in a desired manner. Further details with regard to prodrugs can be found, for example, in Fleisher et al., Advanced Drug Delivery Reviews 19 (1996) 115-130; Design of Prodrugs, H. Bundgaard, Ed., Elsevier, 1985; or H. Bundgaard, Drugs of the Future 16 (1991) 443. Prodrugs which are especially suitable for the compounds of the formula I are ester prodrugs of carboxylic acid groups, amide prodrugs of carboxylic acid groups and alcohol prodrugs of carboxylic acid groups as well as acyl prodrugs and carbamate prodrugs of acylatable nitrogen-containing groups such as amino groups, amidino groups and guanidino groups. In the acyl prodrugs or carbamate prodrugs, a hydrogen atom which is located on a nitrogen atom is replaced with an acyl group or carbamate group. Examples of ester prodrugs and amide prodrugs which may be prepared from the carboxylic acid group in a compound of formula I and which may be mentioned are $(C_1-C_4)$-alkyl esters such as methyl esters, ethyl esters, n-propyl esters, isopropyl esters, n-butyl esters and isobutyl esters, substituted alkyl esters such as hydroxyalkyl esters, acyloxyalkyl esters, aminoalkyl esters, acylaminoalkyl esters and dialkylaminoalkyl esters, unsubstituted amides and N—($C_1$-$C_4$)-alkylamides, such as methylamides or ethylamides. For example the methyl and ethyl esters of the compounds listed above are included.

Alkyl radicals may be straight-chain or branched. This also applies if they carry substituents or occur as substituents of other radicals, for example in alkylamino, alkoxy, arylalkyl, heteroarylalkyl, fluoroalkyl or —S-alkyl radicals. Examples of alkyl radicals are methyl, ethyl, n-propyl, isopropyl (=1-methylethyl), n-butyl, isobutyl (=2-methylpropyl), sec-butyl (=1-methylpropyl), tert-butyl (=1,1-dimethylethyl), pentyl or hexyl. Preferred alkyl radicals are methyl, ethyl, n-propyl, isopropyl, tert-butyl and isobutyl. Where indicated, one or more, for example 1, 2, 3, 4, 5, 6, 7, 8, 9, 10, 11, 12 or 13, hydrogen atoms in alkyl radicals may be replaced by fluorine atoms to form fluoroalkyl radicals. Examples of such radicals are difluoromethyl, trifluoromethyl, pentafluoroethyl, 2,2,2-trifluoroethyl; 3,3,3-trifluoropropyl; 3,3,3-trifluorobutyl, 4,4,4-trifluorbutyl.

Examples of cycloalkyl radicals are cyclopropyl, cyclobutyl, cyclopentyl, cyclohexyl, cycloheptyl or cyclooctyl, in particular cyclopentyl or cylcohexyl. Cycloalkyl radicals can be saturated or partly unsaturated, especially when they are condensed to an aryl or heteroaryl radical. For example a cycloalkyl radical may contain zero, one or two double bonds. This also applies if they carry substituents or occur as substituents of other radicals, for example in the radical cycloalkylalkyl. One or more, for example 1, 2, 3, 4, 5, 6, 7, 8, 9, 10, 11, 12 or 13, hydrogen atoms in cycloalkyl radicals may be replaced by fluorine atoms to form fluorocycloalkyl radicals. Substituted cycloalkyl radicals may be substituted in identical or different positions. Where for a cycloalkylalkyl or cycloalkylalkoxy radical the number of carbon atoms has been given, this is the sum of the number of the carbon atoms in the cycloalkyl and in the alkyl or alkoxy radical, respectively.

Heterocycle radicals are, if not indicated otherwise, monocyclic or bicyclic saturated or partly unsaturated 5, 6, 7, 8, 9 or 10-membered ring compounds in which one or more ring atoms are oxygen atoms, sulfur atoms or nitrogen atoms, e.g. 1, 2 or 3 nitrogen atoms, 1 or 2 oxygen atoms, 1 or 2 sulfur atoms or a combination of various heteroatoms, in particular two oxygen atoms. Heterocycle radicals includes heterocycloalkyls and heterocycloalkenyls and, therefore, they can be saturated or partly unsaturated. Where indicated, a heterocycle may be condensed to an aryl or heteroaryl radical, for example to form 2,3-Dihydro-benzo[1,4]dioxine. For example a heterocycle radical may contain zero, one or two double bonds. The heterocycle radicals may be attached by all positions, for example by the 1 position, 2 position, 3 position, 4 position, 5 position, 6 position, 7 position or 8 position. Heterocycle radicals may be unsubstituted or be substituted one or more times, for example once, twice or three times, by identical or different radicals in identical or different positions. This applies likewise to heterocycle radicals such as, for example, in the radical heterocycloalkyl. Examples of heterocycles are oxirane, aziridine, tetrahydrofurane, tetrahydropyrane, dioxolane, for example 1,3-dioxolane, dioxane, for example 1,4-dioxan, piperidine, pyrrolidin, imidazolidine, triazolidine, hexahydropyrimidine, piperazine, tetrahydropyridazine, triazinane, for example, 1,3,5-triazinane, 1,2,3-triazinane or 1,2,4-triazinane, tetrahydrothiophene, tetrahydrothiopyrane, dithiolane, for example 1,3-dithiolane, dithiane, thiazolidine, oxazolidine, oxathiolane, for example 1,3-oxathiolane, morpholine or thiomorpholine, in particular piperidine, 1,3-dioxolane and 1,4-dioxane.

The aryl radicals are chosen from phenyl, 1-naphthyl, 2-naphthyl and indenyl. Aryl radicals may be unsubstituted or be substituted one or more times, for example once, twice or three times, by identical or different radicals. If a aryl radical is substituted, it preferably has one, two or three identical or different substituents. This likewise applies to substituted aryl radicals in groups such as, for example, arylalkyl or aryloxy. Where indicated, aryl radicals may be condensed to a cycloalkyl or heterocycle radical, for example to form 2,3-Dihydro-benzo[1,4]dioxine, Benzo[1,3]dioxole or indane.

Heteroaryl radicals are monocyclic or bicyclic aromatic 5, 6, 7, 8, 9 or 10-membered ring compounds or, where indicated, 5 or 6 membered ring compounds, in which one or more ring atoms are oxygen atoms, sulfur atoms or nitrogen atoms, e.g. 1, 2 or 3 nitrogen atoms, 1 or 2 oxygen atoms, 1 or 2 sulfur atoms or a combination of various heteroatoms. The heteroaryl radicals may be attached by all positions, for example by the 1 position, 2 position, 3 position, 4 position, 5 position, 6 position, 7 position or 8 position. Heteroaryl radicals may be unsubstituted or substituted one or more times, for example once, twice or three times, by identical or different radicals. This applies likewise to heteroaryl radicals such as, for example, in the radical heteroarylalkyl. Where indicated, heteroaryl radicals may be condensed to a cycloalkyl or heterocycle radical. Examples of heteroaryl having 5 or 6 atoms are furyl, thienyl, pyrrolyl, imidazolyl, pyrazolyl, oxazolyl, isoxazolyl, thiazolyl, isothiazolyl, pyridyl, triazolyl, oxadiazolyl, thiadiazolyl, pyrazinyl, pyrimidinyl, pyridazinyl, tetrazolyl. Examples of other heteroaryls with more atoms are benzothiophenyl, benzofuranyl, indolyl, isoindolyl, indazolyl, quinolyl, isoquinolyl, benzimidazolyl, benzothiazolyl, benzoxazolyl, benzotriazolyl, benzoxadiazolyl, benzothiadiazolyl, quinoxalinyl, quinazolinyl, cinnolinyl, phthalazinyl, quinolizinyl, purinyl, pteridinyl and thienothiazolyl. Also encompassed are the corresponding N-oxides and S-dioxides of these compounds.

When any variable (e.g. aryl, R1) occurs more than one time in any constituent, its definition on each occurrence is independent of its definition at every other occurrence. Also, combinations of substituents and/or variables are permissible only if such combinations result in stable compounds.

The invention further relates to the following processes for preparing the compounds of the formula I.

Compounds of formula I can be prepared as described in Scheme 1

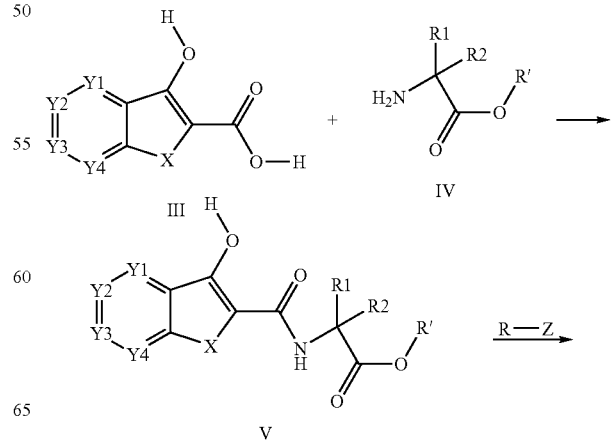

Scheme 1

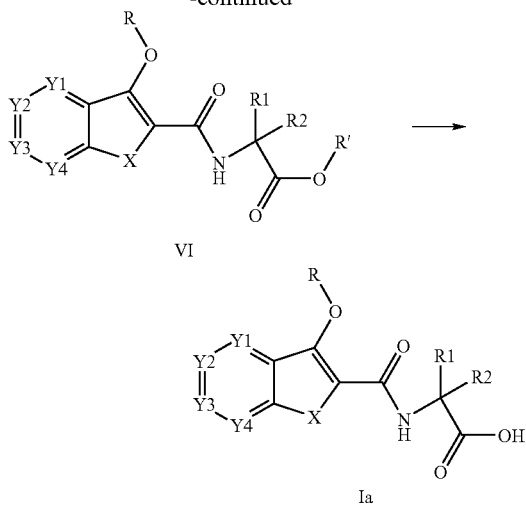

which comprises
a) coupling of an acid of formula III with an amino compound of formula IV to an amide of formula V,
b) reacting a compound of formula V with an reagent R-Z to an compound of formula VI,
c) converting an ester of formula VI to an acid of formula Ia
wherein in the compounds of the formulae Ia, III, IV, V and VI
X, Y1 to Y4, R1 and R2 are defined as in formula I,
R is —C(R11R12)-A, wherein R11, R12 and A are defined as in formula I and
B is —O—(CR11R12)-,
Z is OH or L, wherein L is a leaving group, which can undergo nucleophilic substitution with an amine, and
R' is alkyl having 1, 2, 3, 4, 5 or 6 carbon atoms.

The procedure for preparing the compounds of the formula I is initially a coupling of an amino compound of formula IV with an acid of formula III for preparing the compound of formula V generally in the presence of an coupling agent, for example EDC, DIC or HATU and optionally an additional base, for example triethylamine or Hünig's base, can be used in an appropriate solvent, in particular in an aprotic polar solvent such as, for example, DMF. The reaction temperature in this case is generally from −30° C. to 200° C., preferably from −20° C. to 80°, more preferably from 0° C. to 20° C. The reaction time is generally from 15 min to 6 days, preferably from 15 min to 16 h depending on the composition of the mixture and the chosen temperature range. Subsequently, the transformation of the compound of formula V to the compound of formula VI can be achieved by adding the reagent R-L (Z=L) in the presence of a suitable base, for example potassium or cesium carbonate. L is a leaving group which can undergo nucleophilic substitution, for example Cl, Br, I or OTos. The reaction temperature in this case is generally from −30° C. to 200° C., preferably from 20° C. to 150°. The reaction time is generally from 2 min to 6 days, preferably from 15 min to 16 h, depending on the composition of the mixture and the chosen temperature range. Alternatively the reaction of the compound of formula V with R—OH (Z=OH) can be carried out under Mitsunobu conditions, in the presence of, for example, triphenylphosphine and diethylazodicarboxylate (DEAD) or diphenyl-2-pyridylphoshine and diisopropylazodicarboxylate (DIAD). The reaction temperature in this case is generally from −30° C. to 200° C., preferably from 0° C. to 80°, more preferably from 0° C. to 25° C. The reaction time is generally from 15 min to 6 days, preferably from 15 min to 16 h, depending on the composition of the mixture and the chosen temperature range. The cleavage of the ester of formula VI to the acid of formula Ia in can be achieved in a manner known by the person skilled in the art, for example by the use of a base, like aqueous sodium hydroxide or lithium hydroxide in case of primary or secondary alkyl esters, or for example by the use of an acid, like trifluoroacetic acid in case of tertiary alkyl esters. The reaction temperature in this case is generally from −30° C. to 200° C., preferably from 0° C. to 160° C. The reaction time is generally from 2 min to 6 days, preferably from 2 min to 16 h, depending on the composition of the mixture and the chosen temperature range.

Alternatively compounds of formula I can be prepared as described in Scheme 2

Scheme 2

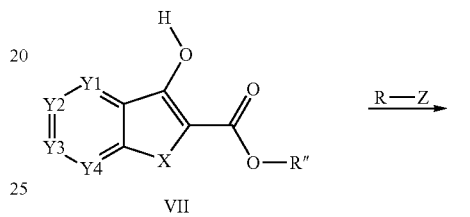

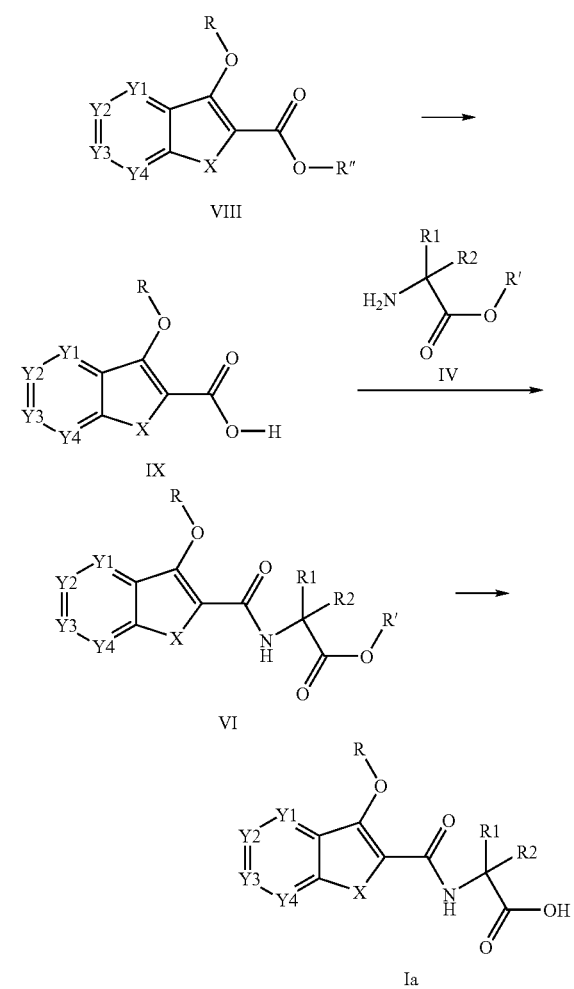

which comprises
a) reacting a compound of formula VII with an reagent R-Z to a compound of formula VII
b) converting an ester of formula VIII to an acid of formula IX
c) coupling of an acid of formula IX with an amino compound of formula IV to an amide of formula VI
d) converting an ester of formula VI to an acid of formula Ia
wherein in the compounds of the formulae Ia, IV, VI, VII, VIII and IX
X, Y1 to Y4, R1 and R2 are defined as in formula I,
R is —(CR11R12)-A, wherein R11, R12 and A are defined as in formula I and
B is —O—(CR11R12)-,
Z is OH or L, wherein L is a leaving group, which can undergo nucleophilic substitution with an amine,
R' is alkyl having 1, 2, 3, 4, 5 or 6 carbon atoms, and
R" is alkyl having 1, 2, 3, 4, 5 or 6 carbon atoms or aryl.

The procedure for preparing the compounds of the formula I is initially a transformation of the compound of formula VII to the compound of formula VIII which can be achieved by adding the reagent R-L (Z=L) in the presence of a suitable base, for example potassium or cesium carbonate. L is a leaving group which can undergo nucleophilic substitution, for example Cl, Br, I or OTos. The reaction temperature in this case is generally from −30° C. to 200° C., preferably from 20° C. to 150°. The reaction time is generally from 2 min to 6 days, preferably from 15 min to 16 h depending on the composition of the mixture and the chosen temperature range Alternatively the reaction of the compound of formula V with R—OH (Z=OH) can be carried out under Mitsunobu conditions, in the presence of, for example, triphenylphosphine and diethylazodicarboxylate (DEAD) or diphenyl-2-pyridylphoshine and diisopropylazodicarboxylate (DIAD). The reaction temperature in this case is generally from −30° C. to 200° C., preferably from 0° C. to 80°, more preferably from 0° C. to 25° C. The reaction time is generally from 15 min to 6 days, preferably from 15 min to 16 h, depending on the composition of the mixture and the chosen temperature range. The subsequent cleavage of the ester of formula VIII to the acid of formula IX can be achieved in a manner known by the person skilled in the art, for example by the use of a base, like aqueous sodium hydroxide or lithium hydroxide, for example in case of primary or secondary alkyl esters, or by the use of an acid, like trifluoroacetic acid, for example in case of tertiary alkyl esters. The reaction temperature in this case is generally from −30° C. to 200° C., preferably from 0° C. to 160° C. The reaction time is generally from 2 min to 6 days, preferably from 2 min to 16 h.

The resulting compound of formula IX can be coupled with the amino compound of formula IV to form the compound of formula VI generally in the presence of an coupling agent, for example EDC, DIC or HATU and optionally an additional base, for example triethylamine or Hünig's base, in an appropriate solvent, in particular in an aprotic polar solvents such as, for example, DMF. The reaction temperature in this case is generally from −30° C. to 200° C., preferably from −20° C. to 80°, more preferably from 0° C. to 20° C. The reaction time is generally from 15 min to 6 days, preferably from 15 min to 16 h, depending on the composition of the mixture and the chosen temperature range. The optional cleavage of the ester of formula VI to the acid of formula Ia in can be achieved as mentioned above, for example by the use of a base, like aqueous sodium hydroxide or lithium hydroxide, for example in case of primary or secondary alkyl esters, or by the use of an acid, like trifluoroacetic acid, for example in case of tertiary alkyl esters. The reaction temperature in this case is generally from −30° C. to 200° C., preferably from 0° C. to 160. The reaction time is generally from 2 min to 6 days, preferably from 2 min to 16 h, depending on the composition of the mixture and the chosen temperature range.

Alternatively, compounds of formula I can be prepared as described in Scheme 3

Scheme 3

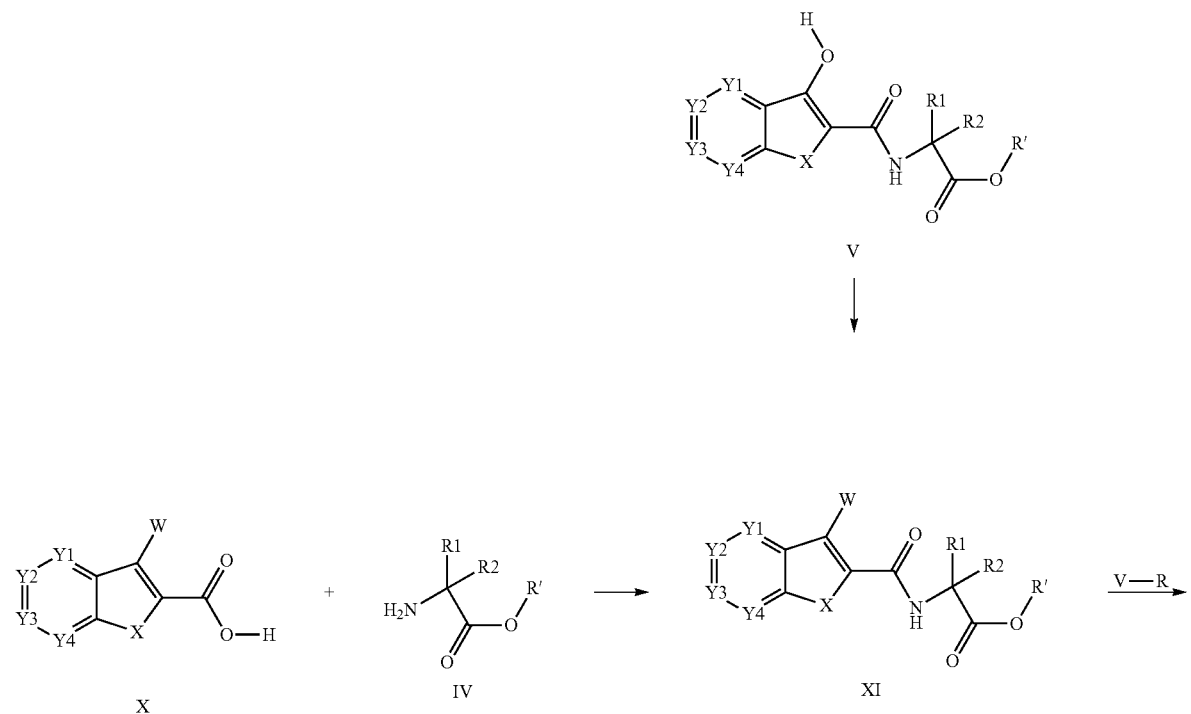

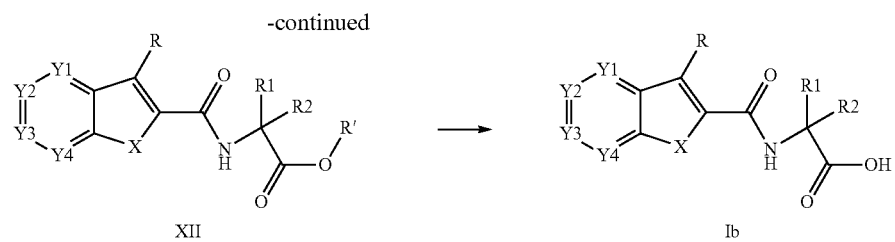

which comprises
a) coupling of an acid of formula X with an amino compound of formula IV to an amide of formula XI,
or, alternatively, the conversion of a compound of formula V to a compound of formula XI (if W is triflate, mesylate or tosylate),
b) reacting a compound of formula XI with an reagent V—R to an compound of formula XI,
c) converting an ester of formula XII to an acid of formula Ib; wherein in the compounds of the formulae Ib, IV, V, X, XI and XII
X, Y1 to Y4, R1 and R2 are defined as in formula I,
V—R is HC≡C-A and R is —C≡C-A,
or V—R is HCR52=CR53-A and R is —CR52=CR53-A,
or V—R is (R'''O)$_2$BCR52=CR53-A and R is —CR52=CR53-A,
or V—R is (R'''')$_3$SnCR52=CR53-A and R is —(R'''')$_3$SnCR52=CR53-A,
or V—R is HalZnCR52=CR53-A and R is —CR52=CR53-A,
or V—R is HNR17-C(R18R19)-A and R is —NR17-C(R18R19)-A,
or V—R is HNR20-C(O)-A and R is —NR20-C(O)-A,
wherein R17, R18, R19, R20, R52, R53 and A are defined as in formula I,
W is halogen, for example 1, Br or Cl, or triflate, mesylate or tosylate,
R' is alkyl having 1, 2, 3, 4, 5 or 6 carbon atoms,
R''' is H or alkyl having 1, 2, 3, 4, 5 or 6 carbon atoms, or alternatively both R''' form, together with the oxygen atoms they are attached to and with the boron atom the oxygen atoms are attached to, a five, six or seven membered ring, which can be unsubstituted or substituted by 1, 2, 3, 4, 5, 6, 7 or 8 alkyl groups,
R'''' is alkyl having 1, 2, 3, 4, 5 or 6 carbon atoms,
Hal is halogen, for example 1, Br or Cl.

The procedure for preparing the compounds of the formula I is initially a coupling of an amino compound of formula IV with an acid of formula X for preparing the compound of formula XI generally in the presence of an coupling agent, for example EDC, DIC or HATU and optionally an additional base, for example triethylamine or Hünig's base, can be used in an appropriate solvent, in particular in an aprotic polar solvent such as, for example, DMF. The reaction temperature in this case is generally from −30° C. to 200° C., preferably from −20° C. to 80°, more preferably from 0° C. to 20° C. The reaction time is generally from 15 min to 6 days, preferably from 15 min to 16 h depending on the composition of the mixture and the chosen temperature range. Alternatively, a compound of formula V can be converted into a compound of formula XI, in which W is defined as triflate, tosylate or mesylate, by reacting it with an anhydride or chloride of trifluoromethane sulfonic acid para-toluene sulfonic acid or methyl sulfonic acid in the presence of a suitable base, for example triethylamine in an appropriate solvent, for example dichloromethane. The reaction temperature in this case is generally from −80° C. to 200° C., preferably from −20° C. to 80°, more preferably from 0° C. to 20° C. The reaction time is generally from 15 min to 6 days, preferably from 15 min to 16 h depending on the composition of the mixture and the chosen temperature range.

Subsequently, the transformation of the compound of formula XI to the compound of formula XII can be achieved by reacting with a reagent V—R, often under inert conditions and in an appropriate solvent, in the presence of a suitable catalytic system, which can contain a palladium and/or copper complex and/or salt, for example Pd$_2$dba$_3$, Pd(Ph$_3$)$_4$, Pd(OAc)$_2$ or CuI, optionally additional ligands as, for example, phosphine, amine or carbene ligands, and optionally auxiliaries like amines, pyridine, quaternary ammonium salts, CsF, Ag$_2$CO$_3$, Na$_2$CO$_3$, K$_2$CO$_3$, Cs$_2$CO$_3$, NaOtBu, KOtBu, NaOAc, KOAc, K$_3$PO$_4$, LiHMDS, NaHMDS or KHMDS. The reaction temperature in this case is generally from −30° C. to 250° C., preferably from 0° C. to 2500, more preferably from 20° C. to 200° C. The reaction time is generally from 15 min to 6 days, preferably from 15 min to 16 h, depending on the composition of the mixture and the chosen temperature range.

The cleavage of the ester of formula XII to the acid of formula Ib can be achieved in a manner known by the person skilled in the art, for example by the use of a base, like aqueous sodium hydroxide or lithium hydroxide in case of primary or secondary alkyl esters, or for example by the use of an acid, like trifluoroacetic acid in case of tertiary alkyl esters. The reaction temperature in this case is generally from −30° C. to 200° C., preferably from 0° C. to 160° C. The reaction time is generally from 2 min to 6 days, preferably from 2 min to 16 h, depending on the composition of the mixture and the chosen temperature range.

Optionally, compounds of formulae Ib and XII in Scheme 3, in which R is defined as —C≡C-A can be (partially) hydrogenated to compounds of formulae Ib and XII, in which R is defined as —CH=CH-A or —CH$_2$CH$_2$-A, and compounds of formulae Ib and XII in Scheme 3, in which R is defined as —CR52=CR53-A can be hydrogenated to compounds of formulae Ib and XII, in which R is defined as —CHR52=CHR53-A. These transformations can be carried out in analogy to the processes which are described in the literature and are known to those skilled in the art, for example by (partial) hydrogenation of said compounds in the presence of homogenous or heterogenous catalysts.

Alternatively compounds of formula I can be prepared as described in Scheme 4

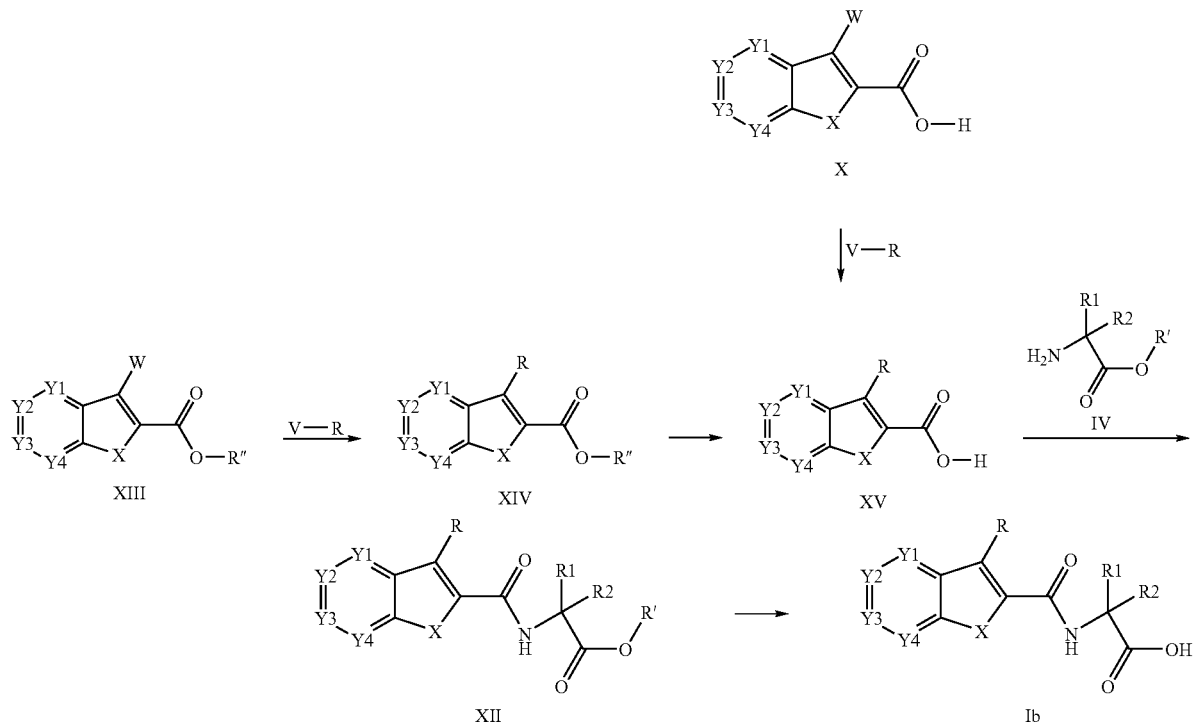

Scheme 4 which comprises
a) reacting a compound of formula XIII with a reagent V—R to a compound of formula XIV
b) converting an ester of formula XIV to an acid of formula XV or, alternatively, reacting a compound of formula X with a reagent V—R to a compound of formula XV
c) coupling of an acid of formula XV with an amino compound of formula IV to an amide of formula XII
d) converting an ester of formula XII to an acid of formula Ib
wherein in the compounds of the formulae Ib, IV, X, XII, XIII, XIV and XV
X, Y1 to Y4, R1 and R2 are defined as in formula I,
V—R is HC≡C-A and R is —C≡C-A,
or V—R is HCR52═CR53-A and R is —CR52═CR53-A,
or V—R is (R'''O)$_2$BCR52═CR53-A and R is —CR52═CR53-A,
or V—R is (R'''')$_3$SnCR52═CR53-A and R is —(R'''')$_3$SnCR52═CR53-A,
or V—R is HalZnCR52═CR53-A and R is —CR52═CR53-A,
or V—R is HNR17-C(R18R19)-A and R is —NR17-C(R18R19)-A,
or V—R is HNR20-C(O)-A and R is —NR20-C(O)-A,
wherein R17, R18, R19, R20, R52, R53 and A are defined as in formula I,
W is halogen, for example I, Br or Cl, or triflate, mesylate or tosylate,
R' is alkyl having 1, 2, 3, 4, 5 or 6 carbon atoms,
R'' is alkyl having 1, 2, 3, 4, 5 or 6 carbon atoms or aryl,
R''' is H or alkyl having 1, 2, 3, 4, 5 or 6 carbon atoms, or alternatively both R''' form, together with the oxygen atoms they are attached to and with the boron atom the oxygen atoms are attached to, a five, six or seven membered ring, which can be unsubstituted or substituted by 1, 2, 3, 4, 5, 6, 7 or 8 alkyl groups,
R'''' is alkyl having 1, 2, 3, 4, 5 or 6 carbon atoms,
Hal is halogen, for example I, Br or Cl.

The procedure for preparing the compounds of the formula I is initially a transformation of the compound of formula XIII to the compound of formula XIV which can be achieved by reacting with a reagent V—R, often under inert conditions and in an appropriate solvent, in the presence of a suitable catalytic system, which can contain a palladium and/or copper complex and/or salt, for example Pd$_2$dba$_3$, Pd(Ph$_3$)$_4$, Pd(OAc)$_2$ or CuI, optionally additional ligands as, for example, phosphine, amine or carbene ligands, and optionally auxiliaries like amines, pyridine, quaternary ammonium salts, CsF, Ag$_2$CO$_3$, Na$_2$CO$_3$, K$_2$CO$_3$, Cs$_2$CO$_3$, NaOtBu, KOtBu, NaOAc, KOAc, K$_3$PO$_4$, LiHMDS, NaHMDS or KHMDS. The reaction temperature in this case is generally from −30° C. to 250° C., preferably from 0° C. to 2500, more preferably from 20° C. to 200° C. The reaction time is generally from 15 min to 6 days, preferably from 15 min to 16 h, depending on the composition of the mixture and the chosen temperature range.

The subsequent cleavage of the ester of formula XIV to the acid of formula XV can be achieved in a manner known by the person skilled in the art, for example by the use of a base, like aqueous sodium hydroxide or lithium hydroxide, for example in case of primary or secondary alkyl esters, or by the use of an acid, like trifluoroacetic acid, for example in case of tertiary alkyl esters. The reaction temperature in this case is generally from −30° C. to 200° C., preferably from 0° C. to 160° C. The reaction time is generally from 2 min to 6 days, preferably from 2 min to 16 h.

Alternatively, a transformation of a compound of formula X to the compound of formula XV can be achieved by reacting with a reagent V—R, often under inert conditions and in an appropriate solvent, in the presence of a suitable catalytic system, which can contain a palladium and/or copper complex and/or salt, for example $Pd_2dba_3$, $Pd(Ph_3)_4$, $Pd(OAc)_2$ or CuI, optionally additional ligands as, for example, phosphine, amine or carbene ligands, and optionally auxiliaries like amines, pyridine, quaternary ammonium salts, CsF, $Ag2CO_3$, $Na_2CO_3$, $K_2CO_3$, $Cs_2CO_3$, NaOtBu, KOtBu, NaOAc, KOAc, $K_3PO_4$, LiHMDS, NaHMDS or KHMDS. The reaction temperature in this case is generally from −30° C. to 250° C., preferably from 0° C. to 2500, more preferably from 20° C. to 200° C. The reaction time is generally from 15 min to 6 days, preferably from 15 min to 16 h, depending on the composition of the mixture and the chosen temperature range.

The resulting compound of formula XV can be coupled with the amino compound of formula IV to form the compound of formula XII generally in the presence of a coupling agent, for example EDC, DIC or HATU and optionally an additional base, for example triethylamine or Hünig's base, in an appropriate solvent, in particular in aprotic polar solvents such as, for example, DMF. The reaction temperature in this case is generally from −30° C. to 200° C., preferably from −20° C. to 80°, more preferably from 0° C. to 20° C. The reaction time is generally from 15 min to 6 days, preferably from 15 min to 16 h, depending on the composition of the mixture and the chosen temperature range. The cleavage of the ester of formula XII to the acid of formula Ib in can be achieved as mentioned above, for example by the use of a base, like aqueous sodium hydroxide or lithium hydroxide, for example in case of primary or secondary alkyl esters, or by the use of an acid, like trifluoroacetic acid, for example in case of tertiary alkyl esters. The reaction temperature in this case is generally from −30° C. to 200° C., preferably from 0° C. to 160. The reaction time is generally from 2 min to 6 days, preferably from 2 min to 16 h, depending on the composition of the mixture and the chosen temperature range. The optional derivatisation of the compounds of the formulae XII or Ib to compounds of formula I, in which D is not defined as C(O)OH, can be carried out in analogy to the processes which are described in the literature and are known to those skilled in the art, for example by reaction of compounds of formula Ia with oxalyl chloride followed by the reaction with a sulfonamide in the presence of a suitable base like sodium hydride.

Optionally, compounds of formulae XIV, XV, XII and Ib in Scheme 4, in which R is defined as —C≡C-A can be (partially) hydrogenated to compounds of formulae XIV, XV, XII and Ib, in which R is defined as —CH═CH-A or —$CH_2CH_2$-A, and compounds of formulae XIV, XV, XII and Ib in Scheme 4, in which R is defined as —CR52═CR53-A can be hydrogenated to compounds of formulae XIV, XV, XII and Ib, in which R is defined as —CHR52═CHR53-A. These transformations can be carried out in analogy to the processes which are described in the literature and are known to those skilled in the art, for example by (partial) hydrogenation of said compounds in the presence of homogenous or heterogenous catalysts.

The compounds of formula Ia and Ib are contained in the compound of formula I.

The starting compounds of the formulae III, IV, V, VII, X and XIII are commercially available or can be prepared by a skilled artisan according to procedures described in the literature.

The workup and optionally the purification of the products and/or intermediates are effected by the customary methods such as extraction, chromatography or crystallization and the customary dryings.

Alternative processes for preparing the compounds are described in the examples and are also part of the invention.

Functional groups in the starting compounds may be present in protected form or in the form of precursors, and then be converted into the desired groups in the compounds of the formula I prepared by the process described above. Corresponding protective group techniques are known to the skilled worker.

It is likewise possible for appropriate functional groups to be derivatized by methods known to the skilled worker.

Another aspect of the invention is the use of a compound of the formula I and/or a pharmaceutically acceptable salt and/or a prodrug thereof alone or in combination with other medicaments or active ingredients as for producing a medicament for the treatment or prophylaxis of chemokine mediated diseases.

The invention further relates to the use of a compound of the formula I and/or a pharmaceutically acceptable salt and/or a prodrug thereof alone or in combination with other medicaments or active ingredients for producing a medicament for the treatment or prophylaxis of a chemokine mediated disease, wherein the chemokine binds to a CXC receptor.

Another aspect of the invention is the use of a compound of the formula I and/or the pharmaceutically acceptable salt and/or a prodrug thereof alone or in combination with other medicaments or active ingredients as for producing a medicament for the treatment or prophylaxis of a chemokine mediated disease, wherein the chemokine binds to a CXCR2 and/or CXCR1 receptor, in particular to a CXCR2 receptor.

The invention further relates to the use of a compound of the formula I and/or a pharmaceutically acceptable salt and/or a prodrug thereof alone or in combination with other medicaments or active ingredients for producing a medicament for the treatment or prophylaxis of rheumatoid arthritis, chronic obstructive pulmonary disease, adult or acute respiratory distress syndrome, asthma, atherosclerosis, myocardial and renal ischemia/reperfusion injury, peripheral limb ischemia/reperfusion injury, inflammatory bowel disease, ulcerative colitis, Crohn's disease, meconium apriration syndrome, atopic dermatitis, cystic fibrosis, psoriasis, psoriatic arthritis, multiple sclerosis, angiogenesis, restenosis, osteoarthritis, osteoporosis, septic shock, endotoxic shock, gram negative sepsis, toxic shock syndrome, stroke, glomerulonephritis, thrombosis, graft vs. host reaction, allograft rejections, transplant reperfusion injury, early transplantation rejection, acute inflammation, alzheimers disease, malaria, respiratory viruses, herpes viruses, hepatitis viruses, HIV, Kaposi's sarcoma-associated viruses, meningitis, gingivitis, herpes encephalitis, CNS vasculitis, traumatic brain injury, brain ischemia/reperfusion injury, migraine, CNS tumors, subarachnoid hemorrhage, post surgical trauma, interstitial pneumonitis, hypersensitivity, crystal induced arthritis, acute and chronic pancreatitis, hepatic ischemia/reperfusion injury, acute alcoholic hepatitis, necrotizing enterocolitis, chronic sinusitis, uveitis, polymyositis, vasculitis, acne, gastric and duodenal ulcers, intestinal ischemia/reperfusion injury, celiac disease, esophagitis, glossitis, rhinitis, airflow obstruction, airway hyperresponsiveness, bronchiolitis, bronchiolitis obliterans, bronchiolitis obliterans organizing pneumonia, bronchiectasis, chronic bronchitis, cor pulmonae, dyspnea, emphysema, hypercapnea, hyperinflation, hyperoxia-induced inflammations, hypoxemia, hypoxia, lung ischemia/reperfusion injury, surgical lung volume reduction, pulmonary fibrosis, pulmonary hypertension, right ventricular hypertrophy, peritonitis associated with continuous ambulatory peritoneal dialysis, granulocytic ehrlichiosis, sarcoidosis, small airway disease, ventilation-perfusion mismatching, wheeze, colds, gout, alcoholic liver disease, lupus, burn therapy, periodontitis, pre-term labor, cough, pruritis, multi-organ dysfunction, trauma, sprains, contusions, undesired hematopoietic stem cell release, angiogenic ocular disease, ocular inflammation, retinopathy or prematurity, diabetic retinopathy, macular degeneration with the wet type preferred and corneal neovasularization, tumor angiogenesis, cancer and metastasis.

In particular, the invention further relates to the use of a compound of the formula I and/or a pharmaceutically acceptable salt and/or a prodrug thereof alone or in combination with other medicaments or active ingredients as for producing a medicament for the treatment or prophylaxis of acute and chronic inflammatory diseases such as atherosclerosis, ischemia/reperfusion injuries, chronic obstructive pulmonary disease, asthma, and rheumatoid arthritis, chemokine (such as, but not limited to IL-8, GRO-α, GRO-β, GRO-γ, NAP-2, ENA-78, or GCP-2) mediated diseases which include adult respiratory distress syndrome, inflammatory bowel disease, ulcerative colitis, Crohn's disease, atopic dermatitis, cystic fibrosis, psoriasis, dermatitis, multiple sclerosis, angiogenesis, restenosis, osteoarthritis, septic shock, endotoxic shock, gram negative sepsis, toxic shock syndrome, stroke, glomerulonephritis, thrombosis, graft vs. host reaction, allograft rejections, alzheimers disease, malaria, viral infections, traumatic brain injury, pulmonary fibrosis, and cancer. In particular, a compound of formula I is used alone.

As a further aspect of the present invention, certain compounds of formula I may have utility as antagonists of the CX3CR1 receptor. Such compounds are expected to be particularly useful in the treatment of disorders within the central and peripheral nervous system and other conditions characterized by an activation of microglia and/or infiltration of leukocytes (e.g. stroke/ischemia and head trauma).

Also claimed is a medicine or pharmaceutical composition for human or veterinary use, comprising an effective amount of a compound of the formula I and/or a pharmaceutically acceptable salt and/or a prodrug thereof, together with pharmaceutically acceptable carriers and additives, alone or in combination with other active pharmaceutical ingredients or medicaments.

Medicaments which comprise a compound of the formula I and/or a pharmaceutically acceptable salt and/or a prodrug thereof can in this connection be administered, for example, orally, parenterally, intravenously, rectally, transdermally or by inhalation, the preferred administration being dependent on the particular characteristics of the disorder. The compounds of the formula I may moreover be used alone or together with pharmaceutical excipients, both in veterinary medicine and in human medicine. The medicaments generally comprise active ingredients of the formula I and/or a pharmaceutically acceptable salt and/or a prodrug thereof in an amount of from 0.01 mg to 1 g per dose unit.

The excipients suitable for the desired pharmaceutical formulation are familiar to the skilled worker on the basis of his expert knowledge. Besides solvents, gel formers, suppository bases, tablet excipients, and other active ingredient carriers, it is possible to use, for example, antioxidants, dispersants, emulsifiers, antifoams, flavorings, preservatives, solubilizers or colors.

For a form for oral administration, the active compounds are mixed with additives suitable for this purpose, such as carriers, stabilizers or inert diluents, and converted by conventional methods into suitable dosage forms such as tablets, coated tablets, hard gelatin capsules, aqueous, alcoholic or oily solutions. Examples of inert carriers which can be used are gum arabic, magnesia, magnesium carbonate, potassium phosphate, lactose, glucose or starch, especially corn starch. It is moreover possible for the preparation to take place both as dry granules and as wet granules. Examples of suitable oily carriers or solvents are vegetable or animal oils such as sunflower oil or fish liver oil.

For subcutaneous, intramuscular or intravenous administration, the active compounds used are converted, if desired with the substances customary for this purpose, such as solubilizers, emulsifiers or other excipients, into a solution, suspension or emulsion. Examples of suitable solvents are: water, physiological saline or alcohols, e.g. ethanol, propanol, glycerol, as well as sugar solutions such as glucose or mannitol solutions, or else a mixture of the various solvents mentioned.

Suitable as pharmaceutical formulation for administration in the form of aerosols or sprays are, for example, solutions, suspensions or emulsions of the active ingredient of the formula I and/or a pharmaceutically acceptable salt and/or a prodrug thereof in a pharmaceutically acceptable solvent such as, in particular, ethanol or water, or a mixture of such solvents. The formulation may, if required, also contain other pharmaceutical excipients such as surfactants, emulsifiers and stabilizers, and a propellant gas. Such a preparation normally contains the active ingredient in a concentration of about 0.1 to 10, in particular of about 0.3 to 3% by weight.

The dosage of the active ingredient of the formula I to be administered, and the frequency of administration, depend on the potency and duration of action of the compounds used; additionally also on the nature and severity of the disorder to be treated and on the sex, age, weight and individual responsiveness of the mammal to be treated.

On average, the daily dose of a compound of the formula I and/or a pharmaceutically acceptable salt and/or a prodrug thereof for a patient weighing about 75 kg is at least 0.001 mg/kg, preferably 0.01 mg/kg, to a maximum of 50 mg/kg, preferably 1 mg/kg, of body weight. For acute episodes of the disorder, for example immediately after suffering a myocardial infarction, higher and, in particular, more frequent dosages may also be necessary, e.g. up to 4 single doses a day. Up to 700 mg a day may be necessary, in particular on i.v. administration, for example for a patient with infarction in the intensive care unit, and the compounds of the invention can be administered by infusion.

List of Abbreviations:

| | |
|---|---|
| O-(7-Azabenzotriazol-1-yl)-N,N,N',N'-tetramethyluronium Hexafluorophosphate | HATU |
| [2-(1H)-benzotriazol-1yl]-1,1,3,3-tetramethyluronium tetra-fluoroborate | TBTU |
| N-Brom-succinimide | NBS |
| Dichloromethane | DCM |
| 4-Dimethylaminopyridine | DMAP |
| Diethylazodicarboxylate | DEAD |
| Diisoppropylazodicarboxylate | DIAD |
| N,N'-Diisopropylcarbodiimid | DIC |
| 1-(3-Dimethylaminopropyl)-3-ethylcarbodiimide-Hydrochloride | EDC |
| N,N-Dimethylformamide | DMF |
| Electron spray ionisation Positive mode | ESI+ or ESI |
| Electron spray ionisation Negative mode | ESI– |
| Tetrahydrofuran | THF |
| N,N,N',N'-Tetramethylethylendiamine | TMEDA |
| Retention time | Rt |

The following examples are part of and intended to illustrate but not limit the present invention.

DESCRIPTION OF THE EXPERIMENTS AND EXAMPLES

Example 1

4-{[1-(4-Trifluoromethyl-benzyloxy)-naphthalene-2-carbonyl]-amino}-tetrahydro-thiopyran-4-carboxylic acid

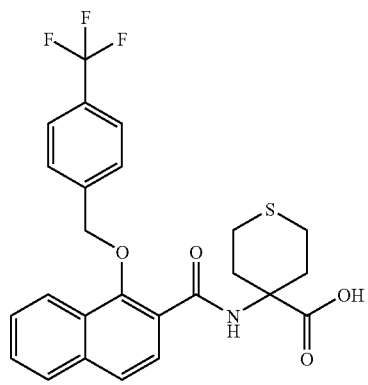 [SMILES: O=C(NC1(C(=O)O)CCSCC1)c1ccc2ccccc2c1OCc1ccc(C(F)(F)F)cc1]

a) 4-[(1-Hydroxy-naphthalene-2-carbonyl)-amino]-tetrahydro-thiopyran-4-carboxylic acid methyl ester To a solution of 0.50 g 1-hydroxy-2-naphthoic acid in 5 ml abs. DMF under inert atmosphere 0.18 g 1-hydroxybenzotriazole, 0.71 g 1-ethyl-3-(3-dimethylaminopropyl)carbodiimide hydrochloride and 0.7 ml N,N-diisopropylethylamine were added. After 15 minutes 0.62 g 4-amino-tetrahydro-thiopyran-4-carboxylic acid methyl ester hydrochloride, followed by 0.55 ml N,N-diisopropylethylamine were added. After 16 h at room temperature and 5 h at 60° C. the reaction was poured unto water, adjusted to pH2 with 2 M HCl and extracted with ethyl acetate twice. The combined organic layers were washed with 2M HCl, 2M aqueous sodium carbonate solution and brine. The organic layer was dried over magnesium sulphate, and concentrated to yield 0.92 g of 4-[(1-hydroxy-naphthalene-2-carbonyl)-amino]-tetrahydro-thiopyran-4-carboxylic acid methyl ester.

$C_{18}H_{19}NO_4S$ (345.42), LCMS (ESI): 346.08 (MH$^+$).

b) 4-{[1-(4-Trifluoromethyl-benzyloxy)-naphthalene-2-carbonyl]-amino}-tetrahydro-thiopyran-4-carboxylic acid methyl ester To 1170 mg caesium carbonate and 310 mg 4-[(1-hydroxy-naphthalene-2-carbonyl)-amino]-tetrahydro-thiopyran-4-carboxylic acid methyl ester in 5 ml abs. DMF 198 mg 1-bromomethyl-4-trifluoromethyl-benzene and 13 mg sodium iodide were added. After 48 h at room temperature the reaction was poured unto ice water and extracted with ethyl acetate twice. The combined organic layers were washed with brine, dried over magnesium sulphate and concentrated in vacuo. After purification by RP-HPLC 380 mg of 4-{[1-(4-trifluoromethyl-benzyloxy)-naphthalene-2-carbonyl]-amino}-tetrahydro-thiopyran-4-carboxylic acid methyl ester were obtained.

$C_{26}H_{24}F_3NO_4S$ (503.54), LCMS (ESI): 504.08 (MH$^+$).

c) 4-{[1-(4-Trifluoromethyl-benzyloxy)-naphthalene-2-carbonyl]-amino}-tetrahydro-thiopyran-4-carboxylic acid 126 mg 4-{[1-(4-trifluoromethyl-benzyloxy)-naphthalene-2-carbonyl]-amino}-tetrahydro-thiopyran-4-carboxylic acid methyl ester in 2.5 ml THF, 0.25 ml 2 M sodium hydroxide and 0.25 ml methanol were reacted at room temperature for 16 h. The reaction was then acidified with 2 M hydrochloric acid and extracted with ethyl acetate twice. The combined organic layers were dried over magnesium sulphate, and concentrated to yield 115 mg of 4-{[1-(4-trifluoromethyl-benzyloxy)-naphthalene-2-carbonyl]-amino}-tetrahydro-thiopyran-4-carboxylic acid.

$C_{25}H_{22}F_3NO_4S$ (489.52), LCMS (ESI): 490.12 (MH$^+$).

Example 2

1-{[1-(4-Trifluoromethyl-benzyloxy)-naphthalene-2-carbonyl]-amino}-cyclopent-3-enecarboxylic acid

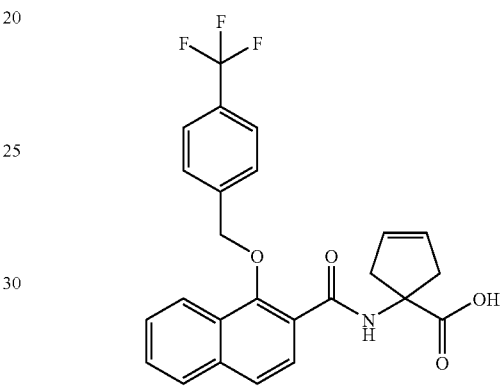

a) 1-(4-Trifluoromethyl-benzyloxy)-naphthalene-2-carboxylic acid methyl ester

To 3.26 g caesium carbonate and 1.01 g methyl 1-hydroxy-2-naphthoate in 10 ml abs. DMF was added 1.21 g 1-bromomethyl-4-trifluoromethyl-benzene and the mixture was reacted for 3 h at room temperature. The reaction was partitioned between water and ethyl acetate and the aqueous layer was extracted with ethyl acetate twice. The combined organic phases were dried over magnesium sulphate and concentrated in vacuo. The resulting residue was purified by chromatography (silica, heptane) to yield 1.62 g of 1-(4-trifluoromethyl-benzyloxy)-naphthalene-2-carboxylic acid methyl ester.

$C_{20}H_{15}F_3O_3$ (360.34), LCMS (ESI): 361.05 (MH$^+$).

b) 1-(4-Trifluoromethyl-benzyloxy)-naphthalene-2-carboxylic acid

To 1.59 g of 1-(4-trifluoromethyl-benzyloxy)-naphthalene-2-carboxylic acid methyl ester were added 10 ml of 2 M aqueous sodium hydroxide and 10 ml of methanol. After 3 h at reflux the mixture was poured unto water, treated with 2 M hydrochloric acid, and three times extracted with ethyl acetate. The combined organic layers were dried over magnesium sulphate and concentrated in vacuo. The resulting residue was purified by crystallization from pentane to yield 1.22 g of 1-(4-trifluoromethyl-benzyloxy)-naphthalene-2-carboxylic acid.

$C_{19}H_{13}F_3O_3$ (346.31), LCMS (ESI): 347.05 (MH$^+$).

c) 1-{[1-(4-Trifluoromethyl-benzyloxy)-naphthalene-2-carbonyl]-amino}-cyclopent-3-enecarboxylic acid methyl ester To a solution of 200 mg 1-(4-trifluoromethyl-benzyloxy)-naphthalene-2-carboxylic acid in 2 ml abs. DMF under inert atmosphere 72 mg 1-hydroxybenzotriazole, 285 mg 1-ethyl- 3-(3-dimethylaminopropyl)carbodiimide hydrochloride and 288 µl of N,N-diisopropylethylamine were added at 0° C. After 30 minutes at 0° C. 229 mg of 1-amino-cyclopent-3-enecarboxylic acid methyl ester hydrochloride, followed by 223 µl of N,N-diisopropylethylamine were added. After 16 h at room temperature the reaction mixture was concentrated, the residue was taken up in ethyl acetate and washed with 2 M HCl, aqueous sodium carbonate solution (10%) and brine. The organic layer was dried over magnesium sulphate and concentrated to yield 320 mg of 1-{[1-(4-trifluoromethyl-benzyloxy)-naphthalene-2-carbonyl]-amino}-cyclopent-3-enecarboxylic acid methyl ester.

$C_{26}H_{22}F_3NO_4$ (469.46), LCMS (ESI): 470.55 (MH$^+$).

d) 1-{[1-(4-Trifluoromethyl-benzyloxy)-naphthalene-2-carbonyl]-amino}-cyclopent-3-enecarboxylic acid 316 mg 1-{[1-(4-trifluoromethyl-benzyloxy)-naphthalene-2-carbonyl]-amino}-cyclopent-3-enecarboxylic acid methyl ester in 9 ml THF, 1.6 ml of 2 M lithium hydroxide and 18 ml methanol were reacted at room temperature for 8 h. The organic solvents were then removed in vacuo, and the residue was acidified with 2 M hydrochloric acid and extracted with ethyl acetate twice. The combined organic layers were dried over magnesium sulphate, and concentrated to yield 200 mg of 1-{[1-(4-trifluoromethyl-benzyl-oxy)-naphthalene-2-carbonyl]-amino}-cyclopent-3-enecarboxylic acid.

$C_{25}H_{20}F_3NO_4$ (455.44), LCMS (ESI): 456.45 (MH$^+$).

The following examples were prepared in analogy to example 1 via a sequence of a coupling of a suitable (ortho-) hydroxy-arene-carboxylic acid with a corresponding amino acid ester using coupling reagents as for example EDC/HOBT, EDC/HOAT, DIC/HOBT, HATU, TBTU/DMAP, followed by an alkylation reaction to attach a suitably substituted alkylating agent to the aromatic hydroxy group and finally a basic hydrolysis of the amino acid ester to the free amino acid:

| Example No. | Structure | Chemical Name | ESI+ or ESI− |
|---|---|---|---|
| 3 | 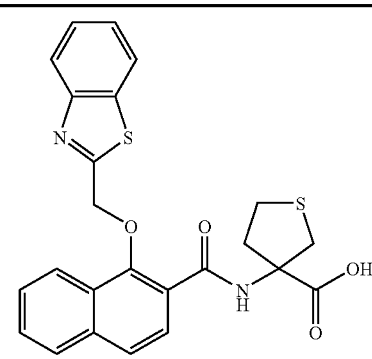 | 3-{[1-(Benzothiazol-2-ylmethoxy)-naphthalene-2-carbonyl]-amino}-tetrahydro-thiophene-3-carboxylic acid | 465.03 |
| 4 | 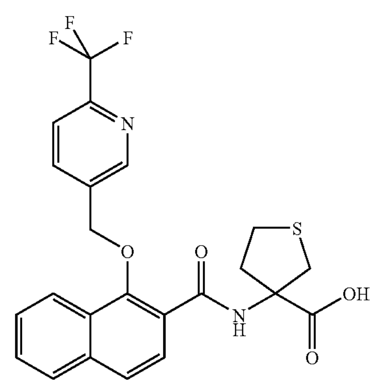 [SMILES: O=C(NC1(C(=O)O)CCSC1)c1ccc2ccccc2c1OCc1ccc(C(F)(F)F)nc1] | 3-{[1-(6-Trifluoromethyl-pyridin-3-ylmethoxy)-naphthalene-2-carbonyl]-amino}-tetrahydro-thiophene-3-carboxylic acid | 477.05 |
| 5 | 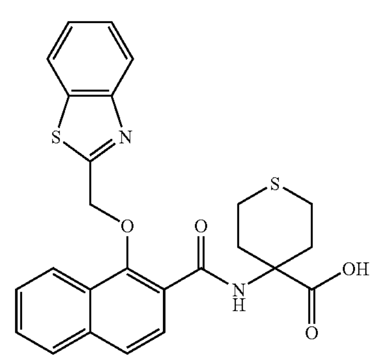 [SMILES: O=C(NC1(C(=O)O)CCSCC1)c1ccc2ccccc2c1OCc1nc2ccccc2s1] | 4-{[1-(Benzothiazol-2-ylmethoxy)-naphthalene-2-carbonyl]-amino}-tetrahydro-thiopyran-4-carboxylic acid | 479.10 |

-continued

| Example No. | Structure | Chemical Name | ESI+ or ESI- |
|---|---|---|---|
| 6 | 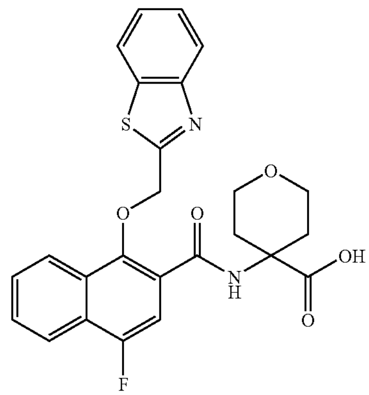 [SMILES: O=C(NC1(C(=O)O)CCOCC1)c1cc(F)c2ccccc2c1OCc1nc2ccccc2s1] | 4-{[1-(Benzothiazol-2-ylmethoxy)-4-fluoro-naphthalene-2-carbonyl]-amino}-tetrahydro-pyran-4-carboxylic acid | 481.09 |
| 7 | 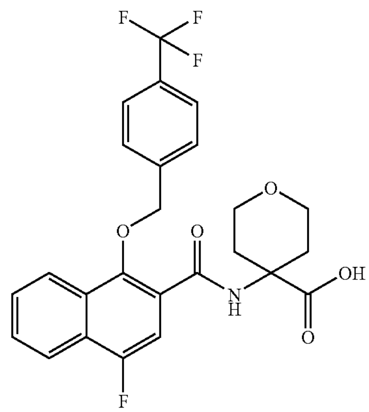 [SMILES: O=C(NC1(C(=O)O)CCOCC1)c1cc(F)c2ccccc2c1OCc1ccc(C(F)(F)F)cc1] | 4-{[4-Fluoro-1-(4-trifluoromethyl-benzyloxy)-naphthalene-2-carbonyl]-amino}-tetrahydro-pyran-4-carboxylic acid | 492.18 |
| 8 | 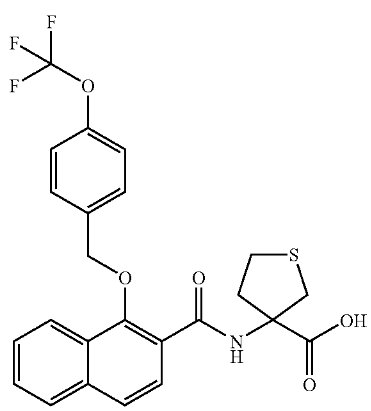 [SMILES: O=C(NC1(C(=O)O)CCSC1)c1ccc2ccccc2c1OCc1ccc(OC(F)(F)F)cc1] | 3-{[1-(4-Trifluoromethoxy-benzyloxy)-naphthalene-2-carbonyl]-amino}-tetrahydro-thiophene-3-carboxylic acid | 492.04 |
| 9 | 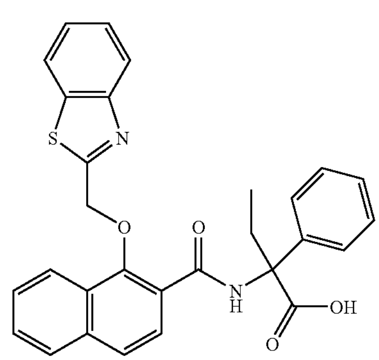 [SMILES: CCC(NC(=O)c1ccc2ccccc2c1OCc1nc2ccccc2s1)(C(=O)O)c1ccccc1] | 2-{[1-(Benzothiazol-2-ylmethoxy)-naphthalene-2-carbonyl]-amino}-2-phenyl-butyric acid | 497.17 |

-continued
| Example No. | Structure | Chemical Name | ESI+ or ESI− |
|---|---|---|---|
| 10 | 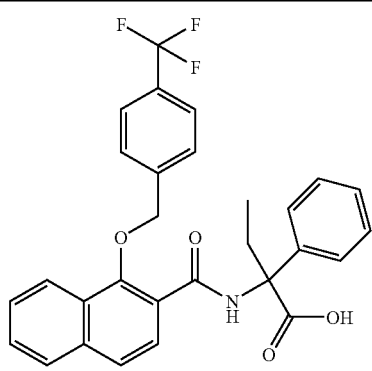 | 2-Phenyl-2-{[1-(4-trifluoromethyl-benzyloxy)-naphthalene-2-carbonyl]-amino}-butyric acid | 508.14 |
| 11 | 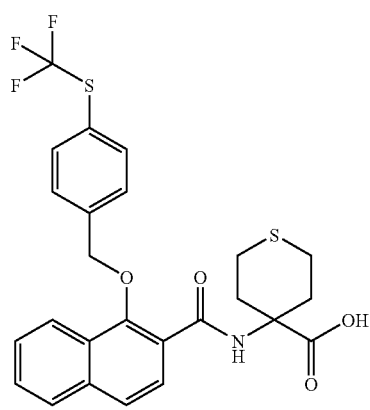 [SMILES: O=C(NC1(C(=O)O)CCSCC1)c1ccc2ccccc2c1OCc1ccc(SC(F)(F)F)cc1] | 4-{[1-(4-Trifluoromethylsulfanyl-benzyloxy)-naphthalene-2-carbonyl]-amino}-tetrahydro-thiopyran-4-carboxylic acid | 522.10 |
| 12 | 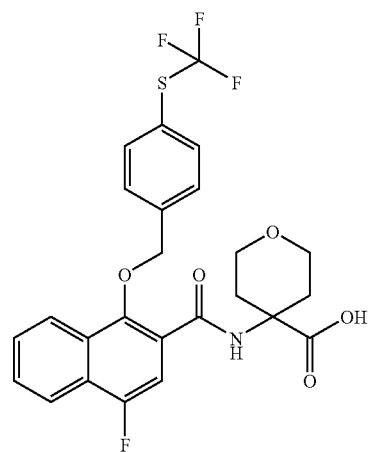 [SMILES: O=C(NC1(C(=O)O)CCOCC1)c1cc(F)c2ccccc2c1OCc1ccc(SC(F)(F)F)cc1] | 4-{[4-Fluoro-1-(4-trifluoromethylsulfanyl-benzyloxy)-naphthalene-2-carbonyl]-amino}-tetrahydro-pyran-4-carboxylic acid | 524.16 |

The following example was prepared in analogy to example 2 via a sequence of an alkylation of a suitable (ortho-)hydroxy-arene-carboxylic ester with a corresponding alkylating agent, followed by a basic hydrolysis of this ester, and a coupling of the resulting acid with a corresponding amino acid ester using coupling reagents as for example EDC/HOBT, DIC/HOBT, HATU, TBTU/DMAP, and finally a basic hydrolysis of the amino acid ester to the free amino acid:

| Example No. | Structure | Chemical Name | ESI+ or ESI− |
|---|---|---|---|
| 13 | 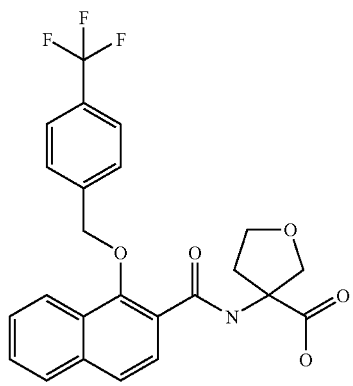 [SMILES: O=C(NC1(C(=O)O)CCOC1)c1ccc2ccccc2c1OCc1ccc(C(F)(F)F)cc1] | 3-{[1-(4-Trifluoromethyl-benzyloxy)-naphthalene-2-carbonyl]-amino}-tetrahydro-furan-3-carboxylic acid | 460.28 |
| 14 | 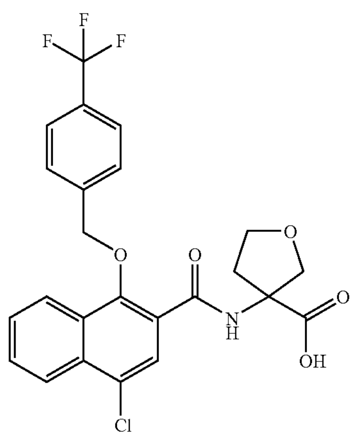 [SMILES: O=C(NC1(C(=O)O)CCOC1)c1cc(Cl)c2ccccc2c1OCc1ccc(C(F)(F)F)cc1] | 3-{[4-Chloro-1-(4-trifluoromethyl-benzyloxy)-naphthalene-2-carbonyl]-amino}-tetrahydro-furan-3-carboxylic acid | 494.00 |

Preparation of Intermediates:
4-Fluoro-1-hydroxynaphthalene-2-carboxylic acid

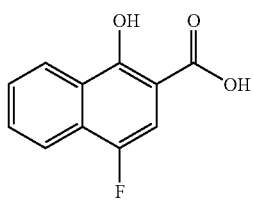 [SMILES: O=C(O)c1cc(F)c2ccccc2c1O]

a) 4-Fluoro-naphthalene-1-carbaldehyde 19.9 g Dichloromethyl methyl ether and 45.7 g tin chloride were dissolved in 70 ml dichloromethane. The solution was cooled to +5° C. and 20.0 g fluoronapthalene in dichloromethane (49 ml) was added over a 60 min period, while keeping the temperature at 5° C. The reaction was brought to room temperature after the addition. After 4 h the reaction was quenched by slowly pouring it into an ice/water mixture. This mixture was stirred for 15 min and left standing overnight. The dichloromethane layer was washed with water, dried (sodium sulphate), filtered through celite and concentrated in vacuo to obtain 24.0 g of 4-fluoro-naphthalene-1-carbaldehyde as an off white solid.

b) 4-Fluoro-naphthalen-1-ol 23.3 g of 4-fluoro-naphthalene-1-carbaldehyde were dissolved in 200 ml dichloromethane. 65.9 g MCPBA was added neat in portions over a 15 min period, 70 ml additional dichloromethane was added and the reaction was stirred overnight at ambient temperature. Then, the reaction mixture was filtered and the solid was washed with dichloromethane. Heptane was added and the mixture filtered several times, then the combined filtrates were concentrated and taken up in ethyl acetate. This was shaken with 10% sodium thiosulfate (100 ml). The organic layer was separated, washed with water and brine, dried over sodium sulphate, filtered and concentrated to yield 27.3 g of the formate ester as a viscous oil, which was dissolved in MeOH (80 ml), treated with KOH (7.5 g) in a methanol solution (30 ml) for 15 min at 5° C. and was then left stirring at ambient temperature for 3 h, before the solvent was removed in vacuo. The resulting oil was treated with 6 M HCl (40 ml) to obtain a pH of 2-3. Water (60 ml) was added) and the aqueous phase was extracted 3× with ethyl acetate (35 ml). The extracts were washed with water (2×20 ml) and concentrated to yield 23.7 g of 4-fluoro-naphthalen-1-ol, which was used without further purification.

c) 4-Fluoro-1-methoxynaphthalene 21.7 g of 4-Fluoro-naphthalen-1-ol were dissolved in 250 ml acetone. 39.0 g of potassium carbonate and 14.6 ml dimethyl sulphate were added at room temperature. The reaction was placed under nitrogen and stirred for 72 h. The mixture was filtrated; the solid washed with acetone, and the filtrate was concentrated to a viscous oil, which was taken up in ethyl acetate. This was washed with water and with brine, dried over sodium sulphate, filtered through celite and concentrated. The resulting oil was distilled using a Kugelrohr-apparatus, yielding 11.4 g of 4-fluoro-1-methoxynaphthalene.

d) 4-Fluoro-1-methoxynaphthalene-2-carbaldehyde 5.25 ml of dichloromethyl methyl ether were dissolved in 40 ml dichloromethane and cooled to +5° C. 6.75 ml tin(IV) chloride were added neat over 45 min to the solution. After the addition the mixture was stirred for 45 min at 5° C. 11.4 g 4-fluoro-1-methoxy-naphthalene in 30 ml dichloromethane was added over 1 h. Then the cooling bath was removed, and the mixture was stirred for 2 h at ambient temperature. It was then poured into ice/water. The dichloromethane layer was separated and the aqueous phase was extracted with dichloromethane. The combined dichloromethane layers were washed with water, dried over sodium sulphate, filtered through celite and concentrated in vacuo. The residue was treated with pentane to yield 9.3 g of 4-fluoro-1-methoxynaphthalene-2-carbaldehyde as a brown solid.

e) 4-Fluoro-1-methoxynaphthalene-2-carboxylic acid 9.3 g of 4-fluoro-1-methoxynaphthalene-2-carbaldehyde were dissolved in 100 ml of acetonitrile. 2.1 g sodium dihydrogenphsophate monohydrate in 10 ml of water were added, followed by the addition of 9.5 ml hydrogen peroxide (30%). 8.9 g sodium chlorite, dissolved in 20 ml water were added drop wise while maintaining an internal temperature between 5° C. and 15° C. The reaction was then allowed to come to room temp over 2.5 h. The precipitated solid was filtered with suction, and the solid was washed with water, and dried in vacuo at 40° C. to yield 9.4 g of 4-fluoro-1-methoxynaphtalene-2-carboxylic acid. The filtrate was treated with 60 ml of cold 10% aqueous sodium bisulfite solution. The aqueous layer was extracted with ethyl acetate. The combined organic layers were washed with water and brine. The organic layer was washed with 0.2 N NaOH twice. The washes were acidified with 6 N HCl to pH 3, whereupon crystallization occurred. The precipitating product was filtered, washed with water and dried in vacuo at 40° C. to yield a second batch of 1.0 g of 4-fluoro-1-methoxynaphthalene-2-carboxylic acid.

f) 4-Fluoro-1-hydroxynaphthalene-2-carboxylic acid

To 10.1 g 4-fluoro-1-methoxynaphthalene-2-carboxylic acid 55 ml HBr/HOAc were added and the mixture was stirred and heated. After 30 min at 60° C. another 7.5 ml of HBr/HOAc were added, and after an additional 30 min at 80° C. the mixture was cooled to ambient temperature and left standing overnight. The reaction was then poured into ice/water and the precipitated solid was filtered and washed with water, followed by 1% ether in heptane and then by heptane. The solid was dried in vacuo at 40° C. to yield 7.7 g 4-fluoro-1-hydroxynaphthalene-2-carboxylic acid.

$C_{11}H_7FO_3$ (206.18), LCMS: (ESI$^+$): 207.2 (MH$^+$).

4-Chloro-1-hydroxy-naphthalene-2-carboxylic acid

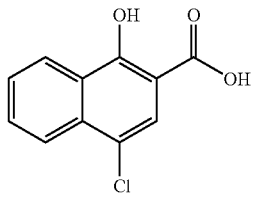 [SMILES: O=C(O)c1cc(Cl)c2ccccc2c1O]

To a suspension of 30.0 g 1-Hydroxy-naphthalene-2-carboxylic acid in 600 ml chloroform a mixture of 14.9 ml sulfuryl chloride and 20 ml chloroform was added dropwise. After stirring the reaction for 8 h at room temperature the precipitated product was isolated by filtration, washed with dichloromethane and recrystallized from isopropanol/water to yield 25.1 g of 4-chloro-1-hydroxy-naphthalene-2-carboxylic acid as off-white solid.

$C_{11}H_7ClO_3$ (222.63, LCMS (ESI): 223.00 (MH$^+$).

The following intermediates were prepared in analogy to the preparation of Example 1, step a) (4-[(1-hydroxy-naphthalene-2-carbonyl)-amino]-tetrahydro-thiopyran-4-carboxylic acid methyl ester) from the corresponding (ortho)-hydroxy-arene-carboxylic acids and the corresponding alpha-amino acid methyl, ethyl or tert-butyl esters using coupling reagents as, for example, EDC/HOBT, EDC/HOAT, DIC/HOBT, HATU, TBTU/DMAP, often in the presence of a base like N,N-diisopropylethylamine:

3-[(1-Hydroxy-naphthalene-2-carbonyl)-amino]-tetrahydro-thiophene-3-carboxylic acid methyl ester

$C_{17}H_{17}NO_4S$ (331.39), LCMS (ESI): 332.10 (MH$^+$).

2-[(1-Hydroxy-naphthalene-2-carbonyl)-amino]-2-phenyl-butyric acid methyl ester

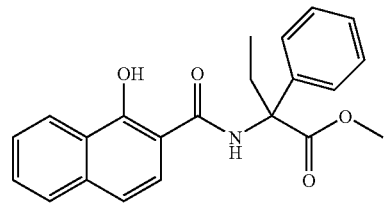 [SMILES: CCC(NC(=O)c1ccc2ccccc2c1O)(C(=O)OC)c1ccccc1]

$C_{22}H_{21}NO_4$ (363.42), LCMS (ESI): 364.14 (MH$^+$).

4-[(4-Fluoro-1-hydroxy-naphthalene-2-carbonyl)-amino]-tetrahydro-pyran-4-carboxylic acid methyl ester

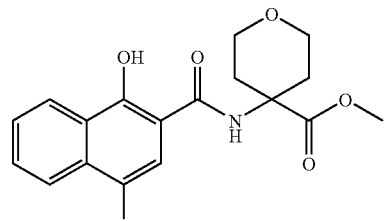

$C_{18}H_{18}FNO_5$ (347.35), LCMS (ESI): 348.1 (MH$^+$).

Determination of CXCR2 Inhibition: Calcium Fluorescence Assay (FLIPR)

The assay is based on the detection of intracellular calcium changes detected by the selective, calcium-chelating dye, Fluo-4 (Molecular Probes). A large fluorescence intensity increase is observed upon calcium association with Fluo-4. The dye is delivered to the cell interior using an acetoxymethylester form of Fluo-4, where the intracellular esterase activity results in the charged species being released and trapped within the cytoplasm of the cell. Hence, influx of calcium to this cytoplasmic pocket, via release from intracellular pools and the phospholipase C cascade can be detected. By co-expressing the CXCR2 receptor and the promiscuous $G_{\alpha16}$ protein, activation of this chemokine receptor is directed into this phospholipase C cascade resulting in intracellular calcium mobilization.

The CHO-K1 cells stably transfected with human CXCR2 and the promiscuous $G_{\alpha16}$ protein were maintained in a log phase of growth at 37° C. and 5% $CO_2$ in the following media: Iscove's, 10% FBS, 1× Penicillin-Streptomycin, 400 µg/mL G418 and 350 µg/mL Zeocin. Approximately 24-48 hours prior to the assay, 20,000-30,000 cells/well were plated onto a 96-well black/clear bottomed assay plate (Becton Dickinson) with a well volume of 180 µl. For dye loading the culture medium was carefully removed and replaced by 100 µl/well dye solution (4 µM Fluo-4 in 135 mM NaCl, 5 mM KCl, 1 mM magnesium sulphate, 5 mM glucose, 20 mM hepes, 2.5 mM probenecid; pH 7.4). Cells were incubated for 1 h at 37° C., and then washed 3× with buffer. After washing 90 µl buffer/well were left. Increasing concentrations of compound was added in 45 µl buffer (4× concentrated) followed by 10 min incubation at 37° C. Then the chemokine (10-100 nM) was applied in 45 µl buffer (4× concentrated) and the measurement performed for 2 min. The IC50 value of a compound was determined by calculation of % inhibition of total calcium response to the chemokine.

Compounds of this invention exhibit activity in the CXCR2-calcium fluorescence (FLIPR) assay in a range of about 0.01 nM to 30000 nM. Some compounds of the invention may additionally exhibit activity as modulators of CXCR1 and CX3CR1. CXCR2 inhibition with chemokine IL-8 for selected example compounds:

| Example No. | IC50 [µM] |
|---|---|
| 10 | 2.2 |
| 12 | 6.0 |

The invention claimed is:
1. A compound of the formula I

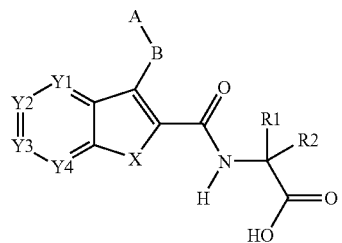

wherein
X is —CR3=CR4-;
R3 and R4, are, independently of one another, hydrogen, F, Cl, Br, I, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 1, 2, 3, 4, 5 or 6 carbon atoms, in which 1, 2, 3, 4, 5, 6, 7, 8, 9, 10, or 11 hydrogen atoms may be substituted by fluorine atoms, alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, —S-alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, OH, CN, $NO_2$, NR27R28, C(O)R29, C(O)NR30R31, $S(O)_O R32$, $S(O)_p$ NR33R34, aryl, heteroaryl, arylalkyl with alkyl having 1, 2, 3 or 4 carbon atoms or heteroarylalkyl with alkyl having 1, 2, 3 or 4 carbon atoms;
R27 is hydrogen or alkyl having 1, 2, 3 or 4 carbon atoms;
R28 is hydrogen, alkyl having 1, 2, 3 or 4 carbon atoms, aryl, C(O)H, C(O)alkyl with alkyl having 1, 2, 3 or 4 carbon atoms or C(O)aryl;
R29 is hydrogen, OH, alkyl with 1, 2, 3 or 4 carbon atoms, alkoxy with 1, 2, 3 or 4 carbon atoms or aryl;
R30, R31, R33 and R34 are, independently of one another, hydrogen, alkyl having 1, 2, 3 or 4 carbon atoms or aryl;
R32 is OH, alkyl having 1, 2, 3 or 4 carbon atoms, alkoxy with 1, 2, 3 or 4 carbon atoms or aryl;
o and p are, independently of one another, 1 or 2;
Y1, Y2, Y3 and Y4 are, independently of one another, —CR8- or nitrogen, with the proviso that at least two of Y1, Y2, Y3 and Y4 are defined as —CR8-;
R8 is hydrogen, F, Cl, Br, I, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 1, 2, 3, 4, 5 or 6 carbon atoms, in which 1, 2, 3, 4, 5, 6, 7, 8, 9, 10, or 11 hydrogen atoms may be substituted by fluorine atoms, alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, —S-alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, OH, CN, $NO_2$, NR36R37, C(O)R38, C(O)NR39R40, $S(O)_q R41$, $S(O)_r NR42R43$, aryl, heteroaryl, arylalkyl with alkyl having 1, 2, 3 or 4 carbon atoms or heteroarylalkyl with alkyl having 1, 2, 3 or 4 carbon atoms;
R36 is hydrogen or alkyl having 1, 2, 3 or 4 carbon atoms
R37 is hydrogen, alkyl having 1, 2, 3 or 4 carbon atoms, aryl, C(O)H, C(O)alkyl with alkyl having 1, 2, 3 or 4 carbon atoms or C(O)aryl;
R38 is hydrogen, OH, alkyl with 1,2,3 or 4 carbon atoms, alkoxy with 1, 2, 3 or 4 carbon atoms or aryl;
R39, R40, R42 and R43 are, independently of one another, hydrogen, alkyl having 1, 2, 3 or 4 carbon atoms or aryl;
R41 is OH, alkyl having 1, 2, 3 or 4 carbon atoms, alkoxy with 1, 2, 3 or 4 carbon atoms or aryl;
q and r are, independently of one another, 1 or 2;
A is cycloalkyl having 3, 4, 5, 6, 7 or 8 carbon atoms, heterocycle, aryl or heteroaryl;
in which the cycloalkyl or heterocycle radical can be condensed to an aryl or heteroaryl radical and in which the cycloalkyl or heterocycle radical and the optionally condensed aryl or heteroaryl radical are unsubstituted or substituted by by 1, 2, 3 or 4 radicals selected from the group consisting of F, Cl, Br, I, OH, CN, $NO_2$, $SF_5$, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 1, 2, 3, 4, 5 or 6 carbon atoms, in which 1, 2, 3, 4, 5, 6, 7, 8, 9, 10 or 11 hydrogen atoms may be substituted by fluorine atoms, alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, —S-alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, —NR9R10, C(O)R44, C(O)N45R46, S(O)$_s$R47, S(O)$_t$NR48R49, —(CH$_2$)$_k$-aryl and —(CH$_2$)$_l$-heteroaryl, in which the aryl and heteroaryl radicals can be substituted by F, Cl, Br, I, alkoxy having 1, 2, 3 or 4 carbon atoms, alkyl having 1, 2, 3 or 4 carbon atoms or O$_a$—(CH$_2$)$_b$—(CF$_2$)$_c$—CF$_3$;

R9 is hydrogen or alkyl having 1, 2, 3 or 4 carbon atoms;

R10 is hydrogen, alkyl having 1, 2, 3 or 4 carbon atoms, aryl, C(O)H, C(O)alkyl having 1, 2, 3 or 4 carbon atoms or C(O)aryl;

R44 is hydrogen, OH, alkyl with 1,2,3 or 4 carbon atoms, alkoxy with 1, 2, 3 or 4 carbon atoms, cycloalkyl having 3, 4, 5 or 6 carbon atoms or aryl;

R45, R46, R48 and R49 are, independently of one another, hydrogen, alkyl having 1, 2, 3 or 4 carbon atoms or aryl;

R47 is OH, alkyl having 1, 2, 3 or 4 carbon atoms, alkoxy with 1, 2, 3 or 4 carbon atoms or aryl;

a is zero or 1;

b, c, k and l are, independently of one another, zero, 1, 2 or 3;

s and t are, independently of one another, 1 or 2;

in which the aryl or heteroaryl radical can be condensed to an cycloalkyl or heterocycle radical and in which the aryl or heteroaryl radical and the optionally condensed cycloalkyl or heterocycle radical are unsubstituted or substituted by 1, 2, 3 or 4 radicals selected from the group consisting of F, Cl, Br, I, OH, CN, NO$_2$, SF5, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 1, 2, 3, 4, 5 or 6 carbon atoms, in which 1, 2, 3, 4, 5, 6, 7, 8, 9, 10 or 11 hydrogen atoms may be substituted by fluorine atoms, alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, —S-alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, —NR9R10, C(O)R44, C(O)N45R46, S(O)$_s$R47, S(O)$_t$NR48R49, —(CH$_2$)$_k$-aryl and —(CH$_2$)$_l$-heteroaryl, in which the aryl and heteroaryl radicals can be substituted by F, Cl, Br, I, alkoxy having 1, 2, 3 or 4 carbon atoms, alkyl having 1, 2, 3 or 4 carbon atoms or O$_a$—(CH$_2$)$_b$—(CF$_2$)$_c$—CF$_3$;

R9 is hydrogen or alkyl having 1, 2, 3 or 4 carbon atoms

R10 is hydrogen, alkyl having 1, 2, 3 or 4 carbon atoms, aryl, C(O)H, C(O)alkyl having 1, 2, 3 or 4 carbon atoms or C(O)aryl;

R44 is hydrogen, OH, alkyl with 1,2,3 or 4 carbon atoms, alkoxy with 1, 2, 3 or 4 carbon atoms, cycloalkyl having 3, 4, 5 or 6 carbon atoms or aryl;

R45, R46, R48 and R49 are, independently of one another, hydrogen, alkyl having 1, 2, 3 or 4 carbon atoms or aryl;

R47 is OH, alkyl having 1, 2, 3 or 4 carbon atoms, alkoxy with 1, 2, 3 or 4 carbon atoms or aryl;

A is zero or 1;

b, c, k and l are, independently of one another, zero, 1, 2 or 3;

s and t are, independently of one another, 1 or 2;

B is —O—C(R11R12)-;

R11 and R12 are hydrogen;

R1 is alkyl having 1, 2, 3, 4, 5 or 6 carbon atoms; which can be unsubstituted or substituted by 1, 2, 3, 4 or 5 radicals selected from the group consisting of F, Cl, Br, I and —O$_i$—(CH$_2$)$_j$—R25;

i is 0 or 1;

j is 0, 1, 2 or 3;

R25 is hydrogen, phenyl, heteroaryl having 5 or 6 atoms, cycloalkyl having 3, 4, 5 or 6 carbon atoms or heterocyclyl having 3, 4, 5, 6, 7 or 8 atoms, in which the phenyl, heteroaryl, cycloalkyl or heterocyclyl are unsubstituted or substituted by 1, 2 or 3 radicals selected from the group consisting of F, Cl, Br and I, and R2 is phenyl, heteroaryl having 5 or 6 atoms, cycloalkyl having 3, 4, 5, 6, 7 or 8 carbon atoms or heterocyclyl having 3, 4, 5, 6, 7 or 8 atoms;

wherein phenyl, heteroaryl having 5 or 6 atoms, cycloalkyl having 3, 4, 5, 6, 7 or 8 carbon atoms or heterocyclyl having 3, 4, 5, 6, 7 or 8 atoms are unsubstituted or substituted by 1, 2, 3, 4 or 5 radicals selected from the group consisting of F, Cl, Br, I, OH, CN, NO$_2$, SCF$_3$, SF$_5$, alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkyl having 3, 4, 5 or 6 carbon atoms, in which 1, 2, 3, 4, 5, 6, 7, 8, 9, 10 or 11 hydrogen atoms may be substituted by fluorine atoms, cycloalkylalkyl having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms, alkoxy having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms, cycloalkoxy having 3, 4, 5 or 6 carbon atoms, in which 1, 2, 3, 4, 5, 6, 7, 8, 9, 10 or 11 hydrogen atoms may be substituted by fluorine atoms and cycloalkylalkoxy having 4, 5, 6, 7 or 8 carbon atoms, in which 1, 2, 3, 4, 5, 6, 7, 8, 9, 10, 11, 12, 13, 14 or 15 hydrogen atoms may be substituted by fluorine atoms;

or R2 is alkyl having 1, 2, 3, 4, 5 or 6 carbon atoms which is substituted by 1, 2, 3, 4 or 5 radicals selected from the group consisting of —O$_m$—(CH$_2$)$_n$-R26;

m is 0 or 1;

n is 0, 1, 2 or 3;

R26 is cycloalkyl having 3, 4, 5 or 6 carbon atoms which is unsubstituted or substituted by 1, 2 or 3 radicals selected from the group consisting of F, Cl, Br and I;

or

R1 and R2 form, together with the carbon atom to which they are attached, a 5- or 6-membered partially unsaturated carbon ring containing one or two double bonds and in which the formed ring can optionally be condensed to phenyl, heteroaryl having 5 or 6 atoms, cycloalkyl having 3, 4, 5, 6,7 or 8 carbon atoms or heterocyclyl having 3, 4, 5, 6, 7 or 8 atoms, wherein the formed ring and the optionally condensed phenyl, heteroaryl, cycloalkyl or heterocyclyl radical can be unsubstituted or substituted by 1, 2, 3, 4 or 5 radicals selected from the group consisting of F, Cl, Br, I, CN, NO$_2$, SCF$_3$, SF$_5$, and alkyl having 1, 2, 3 or 4 carbon atoms;

or

R1 and R2 form, together with the carbon atom to which they are attached, a 4-, 5- or 6-membered carbon ring, wherein one carbon atom, which is not adjacent to the carbon atom to which R1 and R2 are attached, is replaced by —O—, —NR58- or —S(O)$_w$—, and in which the formed ring can be saturated or partially unsaturated, and in which the formed ring can optionally be condensed to phenyl, heteroaryl having 5 or 6 atoms, cycloalkyl having 3, 4, 5, 6,7 or 8 carbon atoms or heterocyclyl having 3, 4, 5, 6, 7 or 8 atoms, wherein the formed ring and the optionally condensed phenyl, heteroaryl, cycloalkyl or heterocyclyl radical can be unsubstituted or substituted by 1, 2, 3, 4 or 5 radicals selected from the group consisting of F, Cl, Br, I, CN, $NO_2$, $SCF_3$, $SF_5$, and alkyl having 1, 2, 3 or 4 carbon atoms;

R58 is hydrogen, alkyl having 1, 2, 3 or 4 carbon atoms or C(O)R59;

R59 is hydrogen, alkyl with 1, 2, 3 or 4 carbon atoms or phenyl;

w is 0, 1 or 2;

or a pharmaceutically acceptable salt or a prodrug thereof.

2. A compound of the formula I as claimed in claim 1, in which

X is —CR3=CR4-,

R3 and R4 are independently of one another, hydrogen, F, Cl, Br, I, alkyl having 1, 2, 3 or 4 carbon atoms or alkoxy having 1, 2, 3 or 4 carbon atoms;

Y1, Y2, Y3 and Y4 are, independently of one another, —CR8- or nitrogen, with the proviso that at least two of Y1, Y2, Y3 and Y4 are defined as —CR8-;

R8 is hydrogen, F, Cl, Br, I or alkyl having 1, 2, 3 or 4 carbon atoms;

A is cycloalkyl having 3, 4, 5, 6, 7 or 8 carbon atoms, heterocycle, aryl or heteroaryl;

in which the cycloalkyl or heterocycle radical can be condensed to an aryl radical and in which the cycloalkyl or heterocycle radical is unsubstituted or substituted by 1, 2 or 3 radicals selected from the group consisting of F, Cl, Br, I, alkyl having 1, 2, 3 or 4 carbon atoms, —C(O)-alkyl having 1, 2, 3 or 4 carbon atoms, —C(O)-cycloalkyl having 3, 4, 5 or 6 carbon atoms and —C(O)O-alkyl having 1, 2, 3 or 4 carbon atoms;

in which the aryl or heteroaryl radical can be condensed to an cycloalkyl or heterocycle radical and in which the aryl or heteroaryl radical is unsubstituted or substituted by 1, 2, 3 or 4 radicals selected from the group consisting of F, Cl, Br, I, CN, $NO_2$, $SF_5$, —NR9R10, alkoxy having 1, 2, 3 or 4 carbon atoms, alkyl having 1, 2, 3, 4, 5 or 6 carbon atoms, —$O_a$—$(CH_2)_b$—$(CF_2)_c$—$CF_3$, —$O_d$—$CHF_2$, —$O_e$—$CH_2F$, —$SO_f$-alkyl having 1, 2, 3 or 4 carbon atoms, S—$(CH_2)_g$—$(CF_2)_h$—$CF_3$, —$(CH_2)_k$-aryl and —$(CH_2)_l$-heteroaryl, in which the aryl and heteroaryl radicals can be substituted by F, Cl, Br, I, $CF_3$, alkoxy having 1, 2, 3 or 4 carbon atoms or alkyl having 1, 2, 3 or 4 carbon atoms;

R9 and R10 are, independently of one another, hydrogen or alkyl having 1, 2, 3 or 4 carbon atoms;

a, d and e are, independently of one another, zero or 1;

b, c, g and h are, independently of one another, zero, 1 or 2;

k and l are, independently of one another, zero, 1, 2 or 3;

f is zero, 1 or 2;

B is —O—(CR11R12)-;

R11 and R12 are hydrogen;

R1 is alkyl having 1, 2, 3, 4, 5 or 6 carbon atoms;

which can be unsubstituted or substituted by 1, 2, 3, 4 or 5 radicals selected from the group consisting of F, Cl, Br, I and —$O_i$—$(CH_2)_j$—R25;

i is 0 or 1;

j is 0, 1, 2 or 3;

R25 is hydrogen, phenyl, heteroaryl having 5 or 6 atoms, cycloalkyl having 3,4,5 or 6 carbon atoms or heterocyclyl having 3, 4, 5, 6, 7 or 8 atoms, in which the phenyl, heteroaryl, cycloalkyl or heterocyclyl are unsubstituted or substituted by 1, 2 or 3 radicals selected from the group consisting of F, Cl, Br and I; and R2 is phenyl, heteroaryl having 5 or 6 atoms, cycloalkyl having 3, 4, 5, 6, 7 or 8 carbon atoms or heterocyclyl having 3, 4, 5, 6, 7 or 8 atoms;

wherein phenyl, heteroaryl having 5 or 6 atoms, cycloalkyl having 3, 4, 5, 6, 7 or 8 carbon atoms or heterocyclyl having 3, 4, 5, 6, 7 or 8 atoms are unsubstituted or substituted by 1, 2, 3, 4 or 5 radicals selected from the group consisting of F, Cl, Br, I, OH, CN, $NO_2$, $SCF_3$, $SF_5$, and alkyl having 1, 2, 3, 4, 5 or 6 carbon atoms, in which 1, 2, 3, 4, 5, 6, 7, 8, 9, 10, 11, 12 or 13 hydrogen atoms may be substituted by fluorine atoms;

or R2 is alkyl having 1, 2, 3, 4, 5 or 6 carbon atoms, which is substituted by —$O_m$—$(CH_2)_n$-R26;

m is 0 or 1;

n is 0, 1, 2 or 3;

R26 is cycloalkyl having 3, 4, 5 or 6 carbon atoms which is unsubstituted or substituted by 1, 2 or 3 radicals selected from F, Cl, Br or I;

or

R1 and R2 form, together with the carbon atom to which they are attached, a 5- or 6-membered partially unsaturated carbon ring containing one or two double bonds and in which the formed ring can optionally be condensed to phenyl, wherein the formed ring and the optionally condensed phenyl, can be unsubstituted or substituted by 1, 2, 3, 4 or 5 radicals selected from the group consisting of F, Cl, Br, I, CN, $NO_2$, $SCF_3$, $SF_5$, and alkyl having 1, 2, 3 or 4 carbon atoms;

or

R1 and R2 form, together with the carbon atom to which they are attached, a 4-, 5- or 6-membered carbon ring, wherein one carbon atom, which is not adjacent to the carbon atom to which R1 and R2 are attached, is replaced by —O—, —NR58- or $S(O)_w$—, and in which the formed ring can be saturated or partially unsaturated, and in which the formed ring can optionally be condensed to phenyl, wherein the formed ring and the optionally condensed phenyl, can be unsubstituted or substituted by 1, 2, 3, 4 or 5 radicals selected from the group consisting of F, Cl, Br, I, CN, $NO_2$, $SCF_3$, $SF_5$, and alkyl having 1, 2, 3 or 4 carbon atoms;

R58 is hydrogen, alkyl having 1, 2, 3 or 4 carbon atoms or C(O)R59;

R59 is hydrogen, alkyl with 1, 2, 3 or 4 carbon atoms or phenyl;

w is 0, 1 or 2;

or a pharmaceutically acceptable salt or a prodrug thereof.

3. A compound of the formula I as claimed in claim 1, in which:

X is —CR3=CR4-,

R3 and R4 hydrogen,

Y1, Y2, Y3 and Y4 are, independently of one another, —CR8- or nitrogen, with the proviso that at least three of Y1, Y2, Y3 and Y4 are defined as —CR8-;

R8 is hydrogen, F or Cl;

A is cyclohexyl or an aryl or heteroaryl radical selected from phenyl, naphthyl, indanyl, thienyl, pyridyl, oxazolyl, isoxazolyl, thiazolyl, imidazolyl, pyrazolyl, pyrazinyl, pyrimidinyl, pyridazinyl, oxadiazolyl, triazolyl, benzothiophenyl, benzoxazolyl, benzothiazolyl or quinolyl;

in which the cyclohexyl is unsubstituted or substituted by 1, 2 or 3 radicals selected from the group consisting of F and alkyl having 1, 2, 3 or 4 carbon atoms;

in which the aryl or heteroaryl radical is unsubstituted or substituted by 1, 2 or 3 radicals selected from the group consisting of F, Cl, Br, CN, $NO_2$, $SF_5$, $-N(CH_3)_2$, methoxy, ethoxy, alkyl having 1, 2, 3 or 4 carbon atoms, $-CF_3$, $-OCF_3$, $-OCH_2CF_3$, $-OCHF_2$, $-SCH_3-$, $-SOCH_3$, $-SO_2CH_3$, $-SCF_3$, phenyl and benzyl; wherein phenyl can be substituted by Cl;

B is $-O-C(R11R12)-$;

R11 and R12 are hydrogen;

R1 is alkyl having 1, 2, 3, 4, 5 or 6 carbon atoms and

R2 is phenyl, heteroaryl having 5 or 6 atoms, cycloalkyl having 3, 4, 5, 6, 7 or 8 carbon atoms or heterocyclyl having 3, 4, 5, 6, 7 or 8 atoms;

wherein phenyl, heteroaryl having 5 or 6 atoms, cycloalkyl having 3, 4, 5, 6, 7 or 8 carbon atoms or heterocyclyl having 3, 4, 5, 6, 7 or 8 atoms are unsubstituted or substituted by 1, 2 or 3 radicals selected from the group consisting of F, Cl, Br, I and alkyl having 1, 2, 3 or 4 carbon atoms;

or R2 is alkyl having 1, 2, 3, 4, 5 or 6 carbon atoms;
which is substituted by $-O_m-(CH_2)_n-R26$;

m is 0 or 1;

n is 0, 1, 2 or 3;

R26 is cycloalkyl having 3, 4, 5 or 6 carbon atoms which is unsubstituted or substituted by 1, 2 or 3 radicals selected from the group consisting of F, Cl, Br and I;

or

R1 and R2 form, together with the carbon atom to which they are attached, a 5- or 6-membered partially unsaturated carbon ring containing one or two double bonds, wherein the formed ring can be unsubstituted or substituted by 1, 2, 3, 4 or 5 radicals selected from the group consisting of F, Cl, Br, I, CN, $NO_2$, $SCF_3$, $SF_5$, and alkyl having 1, 2, 3 or 4 carbon atoms;

or

R1 and R2 form, together with the carbon atom to which they are attached, a 4-, 5- or 6-membered carbon ring, wherein one carbon atom, which is not adjacent to the carbon atom to which R1 and R2 are attached, is replaced by $-O-$, $-NR58-$ or $-S(O)_w-$, and in which the formed ring can be saturated or partially unsaturated, wherein the formed ring can be unsubstituted or substituted by 1, 2, 3, 4 or 5 radicals selected from the group consisting of F, Cl, Br, I, CN, $NO_2$, $SCF_3$, $SF_5$, and alkyl having 1, 2, 3 or 4 carbon atoms;

R58 is hydrogen, alkyl having 1, 2, 3 or 4 carbon atoms or C(O)R59;

R59 is hydrogen, alkyl with 1, 2, 3 or 4 carbon atoms or phenyl;

w is 0, 1 or 2;

or a pharmaceutically acceptable salt or prodrug thereof.

4. A compound of the formula I as claimed in claim 1, in which

X is $-CR3=CR4-$;

R3 and R4 are, independently of one another, hydrogen, F, Cl or Br;

Y1, Y2, Y3 and Y4 are, independently of one another, $-CR8-$;

R8 is hydrogen, F or Cl;

A is cyclohexyl or an aryl or heteroaryl radical selected from the group consisting of phenyl, naphthyl, indanyl, thienyl, pyridyl, thiazolyl, pyrazinyl, pyrimidinyl, pyridazinyl, benzothiophenyl, benzothiazolyl and quinolyl, wherein cyclohexyl is unsubstituted or substituted by 1, 2 or 3 radicals selected from the group consisting of F and alkyl having 1, 2, 3 or 4 carbon atoms, and wherein the aryl or heteroaryl radical is unsubstituted or substituted by 1, 2 or 3 radicals selected from the group consisting of F, Cl, Br, $SF_5$, methoxy, ethoxy, alkyl having 1, 2, 3 or 4 carbon atoms, $CF_3$, $OCF_3$, $OCH_2CF_3$, $OCHF_2$, $SCH_3$, $SCF_3$ and phenyl;

B is $-O-C(R11R12)-$;

R11 is hydrogen;

R12 is hydrogen;

R1 is alkyl having 1, 2, 3 or 4 carbon atoms and

R2 is phenyl, which is unsubstituted or substituted by 1, 2 or 3 radicals selected from the group consisting of F, Cl, Br, I and alkyl having 1, 2, 3 or 4 carbon atoms;

or R2 is methyl or ethyl, which is substituted by $-O_m-(CH_2)_n-R26$;

m is 0 or 1;

n is 0, 1, 2 or 3;

R26 is cycloalkyl having 3, 4, 5 or 6 carbon atoms;

or

R1 and R2 form, together with the carbon atom to which they are attached, a 5- or 6-membered partially unsaturated carbon ring containing one or two double bonds;

or R1 and R2 form, together with the carbon atom to which they are attached, a 4-, 5- or 6-membered carbon ring, wherein one carbon atom, which is not adjacent to the carbon atom to which R1 and R2 are attached, is replaced by $-O-$, $-NH-$ or $-S-$, and in which the formed ring can be saturated or partially unsaturated;

or a pharmaceutically acceptable salt or prodrug thereof.

5. A compound of the formula I as claimed in claim 1, in which

X is $-CR3=CR4-$

R3 and R4 are hydrogen;

Y1, Y2, Y3 and Y4 are $-CH-$;

A is phenyl, pyridyl, or benzothiazolyl, which is unsubstituted or substituted by $-CF_3$, $-OCF_3$, or $SCF_3$;

B is $-O-CH_2-$;

R1 is methyl or ethyl and

R2 is phenyl;

or

R1 and R2 form, together with the carbon atom to which they are attached, a cyclopentene ring;

or

R1 and R2 form, together with the carbon atom, to which they are attached, a tetrahydrothiophene, a tetrahydrothiopyrane, a tetrahydropyrane or a tetrahydrofurane ring; where in said tetrahydrothiophene, tetrahydrothiopyrane, tetrahydropyrane, or tetrahydrofurane, the S or O is not adjacent to the carbon to which R1 and R2 are attached;

or a pharmaceutically acceptable salt or a prodrug thereof.

6. A compound of the formula I as claimed in claim 1 selected from the group consisting of:

4- {[1-(4-Trifluoromethyl-benzyloxy)-naphthalene-2-carbonyl]-amino }-tetrahydro-thiopyran-4-carboxylic acid, 1- {[1-(4-Trifluoromethyl-benzyloxy)-naphthalene-2-carbonyl]-amino }-cyclopent-3-enecarboxylic acid, 3- {[1-(Benzothiazol-2-ylmethoxy)-naphthalene-2-carbonyl]-amino }-tetrahydro-thiophene-3-carboxylic acid, 3- {[1 -(6-Trifluoromethyl-pyridin-3-ylmethoxy)-naphthalene-2-carbonyl]-amino }-tetrahydro -thiophene-3-carboxylic acid, 4- {[1-(Benzothiazol-2-ylmethoxy)-naphthalene-2-carbonyl]-amino }-tetrahydro-thiopyran-4-carboxylic acid, 4- {[1-(Benzothiazol-2-ylmethoxy)-4-fluoro-naphthalene-2-carbonyl]-amino}-tetrahydro-pyran-4-carboxylic acid,
4-{[4-Fluoro-1-(4-trifluoromethyl-benzyloxy)-naphthalene-2-carbonyl]-amino }-tetrahydro -pyran-4-carboxylic acid,
3-{[1-(4-Trifluoromethoxy-benzyloxy)-naphthalene-2-carbonyl]-amino}-tetrahydro-thiophene-3-carboxylic acid,
2-{[1-(Benzothiazol-2-ylmethoxy)-naphthalene-2-carbonyl]-amino }-2-phenyl-butyric acid,
2-Phenyl-2-{[1-(4-trifluoromethyl-benzyloxy)-naphthalene-2-carbonyl]-amino}-butyric acid,
4-{[1-(4-Trifluoromethylsulfanyl-benzyloxy)-naphthalene-2-carbonyl]-amino}-tetrahydro -thiopyran-4-carboxylic acid or
4-{[4-Fluoro- 1-(4-trifluoromethylsulfanyl-benzyloxy)-naphthalene-2-carbonyl]-amino}-tetrahydro-pyran-4-carboxylic acid,
3-{[1-(4-Trifluoromethyl-benzyloxy)-naphthalene-2-carbonyl]amino}-tetrahydro-furan-3-carboxylic acid, and
3-{[4-Chloro-1-(4-trifluoromethyl-benzyloxy)-naphthalene-2-carbonyl]-amino}-tetrahydro -furan-3-carboxylic acid;
or a pharmaceutically acceptable salt or a prodrug thereof.

7. A compound of the formula I or a pharmaceutically acceptable salt or a prodrug thereof as claimed in claim 1 for use as a medicament.

8. A medicine for human, veterinary or phytoprotective use comprising an effective amount of a compound of the formula I or a pharmaceutically acceptable salt or a prodrug thereof as claimed in claim 1, together with pharmaceutically acceptable carriers and additives.

9. A medicine for human, veterinary or phytoprotective use comprising an effective amount of at least one compound of the formula I or a pharmaceutically acceptable salt or a prodrug thereof as claimed in claim 1, together with pharmaceutically acceptable carriers and additives in combination with at least one pharmacological active ingredient or medicament.

10. A method of treating atherosclerosis or melanoma in a subject, the method comprising administering to said subject a therapeutically effective amount of a compound of formula I in claim 1 or a pharmaceutically acceptable salt thereof alone or in combination with other medicaments.

* * * * *